US012674751B2

(12) United States Patent
Choi et al.

(10) Patent No.: US 12,674,751 B2
(45) Date of Patent: Jul. 7, 2026

(54) IMAGING DEVICE FOR CORRECTING AND RECONSTRUCTING TARGET IMAGE IN SCATTERING MEDIUM USING MULTIPLE SCATTERING TRACING ALGORITHM BASED ON REFLECTION MATRIX AND METHOD THEREOF

(71) Applicants: Korea University Research and Business Foundation, Seoul (KR); INSTITUTE FOR BASIC SCIENCE, Daejeon (KR)

(72) Inventors: Won Shik Choi, Seoul (KR); Sung Sam Kang, Seoul (KR); Seok Chan Yoon, Seoul (KR)

(73) Assignees: KOREA UNIVERSITY RESEARCH AND BUSINESS FOUNDATION;, Seoul (KR); INSTITUTE FOR BASIC SCIENCE, Daejeon (KR)

( * ) Notice: Subject to any disclaimer, the term of this patent is extended or adjusted under 35 U.S.C. 154(b) by 151 days.

(21) Appl. No.: 18/828,107

(22) Filed: Sep. 9, 2024

(65) Prior Publication Data

US 2025/0093262 A1    Mar. 20, 2025

(30) Foreign Application Priority Data

Sep. 18, 2023    (KR) ........................ 10-2023-0124023

(51) Int. Cl.
*G01N 21/64*        (2006.01)
*G01N 21/47*        (2006.01)
            (Continued)

(52) U.S. Cl.
CPC ....... *G01N 21/4738* (2013.01); *G01N 33/025* (2013.01); *G01N 33/4833* (2013.01); *G06T 5/80* (2024.01); *G06T 2207/10056* (2013.01)

(58) Field of Classification Search
None
See application file for complete search history.

(56) References Cited

U.S. PATENT DOCUMENTS

2020/0110026 A1*    4/2020    Choi ................. G01B 9/02015
2021/0310787 A1*   10/2021    Aubry ............... G01B 9/02091
2022/0381695 A1    12/2022    Choi et al.

FOREIGN PATENT DOCUMENTS

KR    10-2019-0023324 A    3/2019
KR    10-2020-0131908 A    11/2020
                (Continued)

OTHER PUBLICATIONS

Notice of Reasons for Refusal, dated Mar. 25, 2025, for the corresponding Japanese Patent Application No. 2024-023150, along with a partial English machine translation (4 pages).
                (Continued)

*Primary Examiner* — Hoon K Song
(74) *Attorney, Agent, or Firm* — Hauptman Ham, LLP

(57) ABSTRACT

Disclosed are an imaging device for correcting and reconstructing a target image in a scattering medium using a multiple scattering tracing algorithm based on a reflection matrix and a method thereof. According to an embodiment of the present disclosure, the imaging device corrects and reconstructs an image of a target object located deep inside a scattering medium such as a biological tissue by tracing a multiple scattering trajectory using a time-resolved reflection matrix obtained from an imaging device that uses a time-resolved light source and then correcting it.

14 Claims, 23 Drawing Sheets

(51) Int. Cl.
　　*G01N 33/02* 　　　(2006.01)
　　*G01N 33/483* 　　(2006.01)
　　*G06T 5/80* 　　　(2024.01)

(56) References Cited

FOREIGN PATENT DOCUMENTS

| | | | |
|---|---|---|---|
| KR | 10-2023-0062343 A | 5/2023 | |
| WO | WO-2020157759 A1 * | 8/2020 | ............ G01N 21/47 |
| WO | 2022/012927 A1 | 1/2022 | |

OTHER PUBLICATIONS

[Supportive materials for Exception to Loss of Novelty] Sungsam Kang et al., "Tracing multiple scattering trajectories for deep optical imaging in scattering media", Accessibility Forum 2024, Feb. 19, 2023, 17 Pages, https://arxiv.org/abs/2302.09503.

[Supportive materials for Exception to Loss of Novelty] Sungsam Kang et al., "Session G1-op: Focus: Deep-tissue Optical Imaging", 2023 KPS Spring Meeting, Daejeon Convention Center & IBS SCC, Apr. 19-21, 2023, https://www.kps.or.kr/conference/event/index.php?cfrid=19.

* cited by examiner

IMAGING DEVICE FOR CORRECTING AND RECONSTRUCTING TARGET IMAGE IN SCATTERING MEDIUM USING MULTIPLE SCATTERING TRACING ALGORITHM BASED ON REFLECTION MATRIX AND METHOD THEREOF

CROSS-REFERENCE TO RELATED APPLICATION

This application claims the benefit of priority Korean Patent Application No. 10-2023-0124023, filed on Sep. 18, 2023 in the Korean Intellectual Property Office. The aforementioned application is hereby incorporated by reference in its entirety.

BACKGROUND OF THE DISCLOSURE

Field of the Disclosure

The present disclosure relates to an imaging device for correcting and reconstructing a target image in a scattering medium using a multiple scattering tracing algorithm based on a reflection matrix and a method thereof, and more particularly to a technology of correcting and reconstructing an image of a target object located deep inside a scattering medium such as a biological tissue by tracing a multiple scattering trajectory using a time-resolved reflection matrix obtained from an imaging device that uses a time-resolved light source and then correcting it.

Description of the Related Art

As the depth of biological tissue increases, imaging becomes limited due to multiple scattering caused by the structure of the tissue.

To overcome this, a reflection matrix microscope capable of measuring a time-resolved reflection matrix to suppress multiple scattering was developed.

This manner can use a method of selectively using only ballistic waves propagating without experiencing multiple scattering from among scattering components of light propagating inside a scattering medium.

Meanwhile, a closed loop accumulation of single scattering (CLASS) method was developed to measure and correct the aberration of a scattering medium that distorts these ballistic waves.

A reflection matrix microscope measures the reflection matrix of a scattering medium, and measures the intensity and phase of the electric field of reflected light corresponding to each incident beam (light) using the interference phenomenon of light while changing the angle of incidence of light incident on the scattering medium.

The reflection matrix of the scattering medium is reconstructed from the measured complex phase image in the form of a matrix of an output basis for an input basis.

An image of the object inside the scattering medium is acquired from the reflection matrix, and, if the input basis is the location of an incident beam focus, the object image is acquired using a confocal microscope. If the input basis is the incident angle of the incident beam, the object image is reconstructed using collective accumulation of single scattering (CASS) microscopy. In this process, multiple scattering is suppressed and only ballistic waves are selectively used.

The CLASS microscope uses a method of removing aberration applied to a ballistic wave by finding aberration information from a reflection matrix and post-correcting it.

After converting the time-resolved reflection matrix based on the angles of incidence and reflection, an additional phase delay value is added for each angle of incidence and reflection to maximize the intensity of a final image, thereby correcting the aberration reflected in single scattering.

If the reference of the incident beam is the location of the focus, the same operation can be performed by converting it to the reference angles of incidence and reflection through Fourier transform.

This technology can be used for correction by checking the aberration experienced in the process in which incident light reaches a target object and the aberration experienced in the process in which light reflected by the object is returned.

RELATED ART DOCUMENTS

Patent Documents (Patent Document 1) International Patent Publication No. WO2022/012927, "SPECTROMETRIC METROLOGY SYSTEMS BASED ON MULTIMODE INTERFERENCE AND LITHOGRAPHIC APPARATUS"

(Patent Document 2) Korean Patent Application Publication No. 10-2020-0131908 entitled "AN OVERLAY METROLOGY SYSTEM AND METHOD"

(Patent Document 3) Korean Patent Application Publication No. 10-2023-0062343 entitled "MICROSCOPY SYSTEM BASED ON WAVEFRONT SENSING ADAPTIVE OPTICS FOR SUPER-RESOLUTION IMAGING AND OPERATING METHOD THEREOF"

(Patent Document 4) Korean Patent Application Publication No. 10-2019-0023324 entitled "Imaging system for Obtaining multi-mode images"

SUMMARY OF THE DISCLOSURE

The existing CLASS method focuses only on correcting angle-dependent phase shifts of ballistic waves for image reconstruction and does not utilize multiply scattered waves.

Therefore, the present disclosure has been made in view of the above problems, and it is an object of the present disclosure to provide a device for tracing multiple scattering trajectories using a time-resolved reflection matrix obtained from an imaging device using a time-resolved light source, and then correcting and reconstructing an internal target image located deep inside a scattering medium such as biological tissue by correcting the traced multiple scattering trajectory; and a method thereof.

It is another object of the present disclosure to obtain a time-resolved reflection matrix of the scattering medium, and then reconstruct the trajectory of multiple scattered waves using a numerical iterative technique according to the multiple scattering tracing (MST) algorithm, and reconstruct and correct a target image corresponding to an object inside a scattering medium image using the reverse process of the trajectory of the reconstructed multiple scattering waves.

It is still another object of the present disclosure to have a very wide range of uses for image acquisition in a label-free manner, not to require additional equipment required in an existing reflection matrix microscope, and not to affect the data measurement time itself because it is a post-processing technology. So, it is expected to be used for in-vivo image acquisition that requires rapid measurement, and to be used in research on various disease models or animal experiments, and to provide an imaging device and method that can expand the scope of application to use as a diagnostic and clinical tool.

It is still another object of the present disclosure to provide a post-processing method in which data such as reflection matrix data is acquired and then corrected, and to immediately acquire data without prior preparation, thereby obtaining 3D high-depth images while maintaining the subject's condition in in-vivo imaging as data measurement time is reduced.

It is still another object of the present disclosure to provide an imaging device and method capable of providing various biomedical applications because it can acquire 3D high-depth images while changing a measurement depth along with a reduction in data measurement time.

It is yet another object of the present disclosure to provide an algorithm applied to a reflection matrix obtained through reflection without labeling, and to provide an imaging device that can be directly applied to clinical practice because it can acquire high-depth, high-resolution images, and that can be applied as measurement equipment because it can obtain images of the inside of not only biological tissues but also samples such as semiconductors without disassembling the inside.

In accordance with an aspect of the present disclosure, the above and other objects can be accomplished by the provision of an imaging device, including: a light source configured to make light incident on a target object by passing through a scattering medium and multiple scattering components within the scattering medium; a detector configured to detect light returned after the incident light transmits and reflects the multiple scattering components of the target object; a reflection matrix measurer configured to measure a time-resolved reflection matrix reflecting multiple scattering trajectories based on the multiple scattering components based on the returning light; an algorithm processor configured to obtain an incident transmission matrix and a reflection transmission matrix by numerically iteratively accessing a plurality of phase planes approximated from the scattering medium according to a multiple scattering tracing algorithm and to obtain an object reflection matrix by reflecting inverse matrices of the obtained incident transmission matrix and the obtained reflection transmission matrix into the measured time-resolved reflection matrix; and an image processor configured to acquire an image in which multiple scattering distortion is corrected according to the multiple scattering trajectory based on the obtained object reflection matrix.

The algorithm processor may perform numerical iterative access to each phase plane by multiplying an input or output end of the time-resolved reflection matrix by a spatial propagation matrix ($P_k$) corresponding to a distance to a k-th phase plane based on the multiple scattering tracing algorithm to obtain a plurality of incident transmission matrices and reflection transmission matrices corresponding to the k-th.

In consideration of a case where light is focused on two different points for a specific phase plane among the plural phase planes, the algorithm processor may obtain a difference between phase delay values of the two points based on the multiple scattering tracing algorithm, and apply the obtained difference to an incident transmission matrix and reflection transmission matrix obtained for the specific phase plane.

Each of the plural phase planes may calculate a transmission matrix in relation to the multiple scattering components inside the scattering medium, design a first phase plane based on the calculated transmission matrix, and design a second phase plane on the designed first phase plane based on the inverse transmission matrix of the calculated transmission matrix to be virtually located inside the scattering medium or to be located on the scattering medium.

A location of the plural phase planes may be determined by measuring an electric field intensity through application of the multiple scattering tracing algorithm while changing a distance from the target object, and is determined as a location where the measured electric field intensity is greater than a reference value.

The number of the plural phase planes may be determined by measuring an electric field strength through application of the multiple scattering tracing algorithm while changing the number of phase planes, and may be determined considering a calculation time according to the changed number.

The reflection matrix measurer may determine matrix components as light concentrated at each position on a surface of the target object, and measure the time-resolved reflection matrix determined as an intensity and phase of electric field measured on an output basis at each position of a camera placed on a conjugate image plane of the object surface, resulting in reflected light on an input basis.

The light source may make the light incident as a point light on the target object and change an incident location on the target object by changing a position of the point light.

The detector may detect the changed detection pixel according to the changed incident location.

The algorithm processor may calculate an inverse matrix for each of an incident transmission matrix and reflection transmission matrix associated with phase values for the plural phase planes for the multiple scattering components of the scattering medium according to the multiple scattering tracing algorithm and phase values for plural points respectively constituting the plural phase planes, and may reflect the calculated inverse matrix into the time-resolved reflection matrix to obtain an object reflection matrix for the target object.

In accordance with another aspect of the present disclosure, there is provided an imaging method, including: making, by a light source, light incident on a target object by passing through a scattering medium and multiple scattering components within the scattering medium; detecting, by a detector, light returned after the incident light transmits and reflects the multiple scattering components of the target object; measuring, by a reflection matrix measurer, a time-resolved reflection matrix reflecting multiple scattering trajectories based on the multiple scattering components based on the returning light; obtaining, by an algorithm processor, an incident transmission matrix and a reflection transmission matrix by numerically iteratively accessing a plurality of phase planes approximated from the scattering medium according to a multiple scattering tracing algorithm and obtaining an object reflection matrix by reflecting inverse matrices of the obtained incident transmission matrix and the obtained reflection transmission matrix into the measured time-resolved reflection matrix; and acquiring, by an image processor, an image in which multiple scattering distortion is corrected according to the multiple scattering trajectory based on the obtained object reflection matrix.

The obtaining may include performing numerical iterative access to each phase plane by multiplying an input or output end of the time-resolved reflection matrix by a spatial propagation matrix ($P_k$) corresponding to a distance to a k-th phase plane based on the multiple scattering tracing algorithm to obtain a plurality of incident transmission matrices and reflection transmission matrices corresponding to the k-th.

The obtaining may include obtaining, in consideration of a case where light is focused on two different points for a specific phase plane among the plural phase planes, a difference between phase delay values of the two points based on the multiple scattering tracing algorithm, and applying the obtained difference to an incident transmission matrix and reflection transmission matrix obtained for the specific phase plane.

Each of the plural phase planes may calculate a transmission matrix in relation to the multiple scattering components inside the scattering medium, design a first phase plane based on the calculated transmission matrix, and design a second phase plane on the designed first phase plane based on the inverse transmission matrix of the calculated transmission matrix to be virtually located inside the scattering medium or to be located on the scattering medium.

A location of the plural phase planes may be determined by measuring an electric field intensity through application of the multiple scattering tracing algorithm while changing a distance from the target object, and is determined as a location where the measured electric field intensity is greater than a reference value, and the number of the plural phase planes may be determined by measuring an electric field strength through application of the multiple scattering tracing algorithm while changing the number of phase planes, and may be determined considering a calculation time according to the changed number.

BRIEF DESCRIPTION OF THE DRAWINGS

The above and other objects, features and other advantages of the present disclosure will be more clearly understood from the following detailed description taken in conjunction with the accompanying drawings, in which:

FIG. 5 illustrates a process for designing a plurality of phase planes related to a multiple scattering tracing algorithm based on a reflection matrix in an imaging method according to an embodiment of the present disclosure;

Figure 10A:
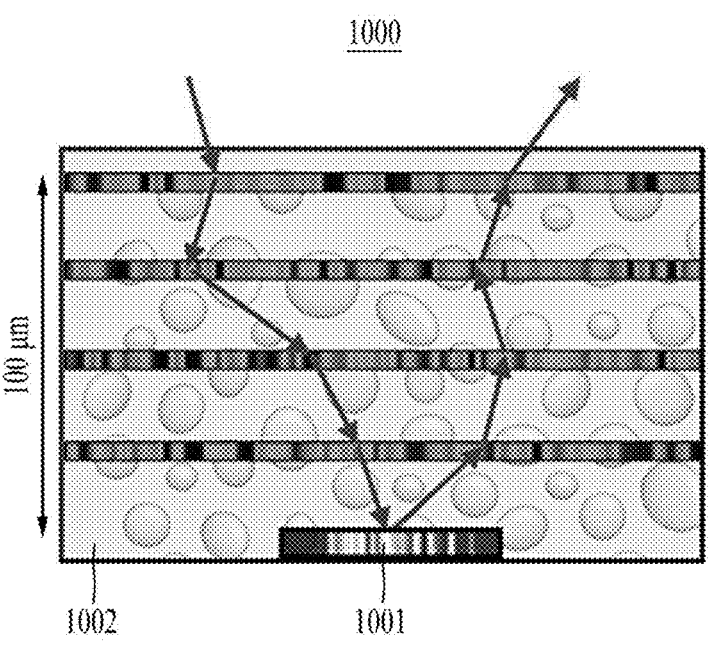
Figure 10A:
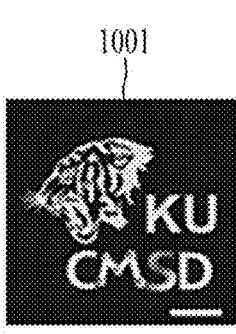
Figure 10B:
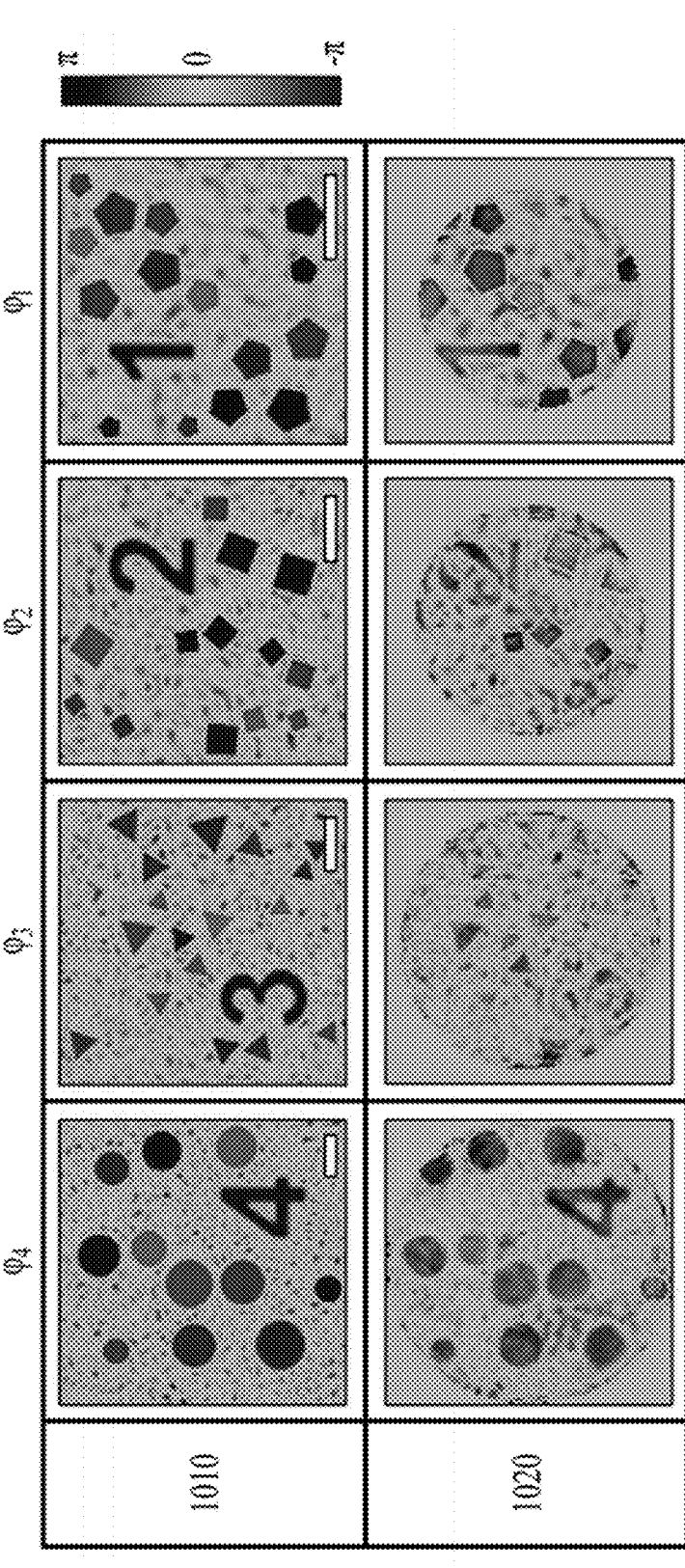
Figure 10C:
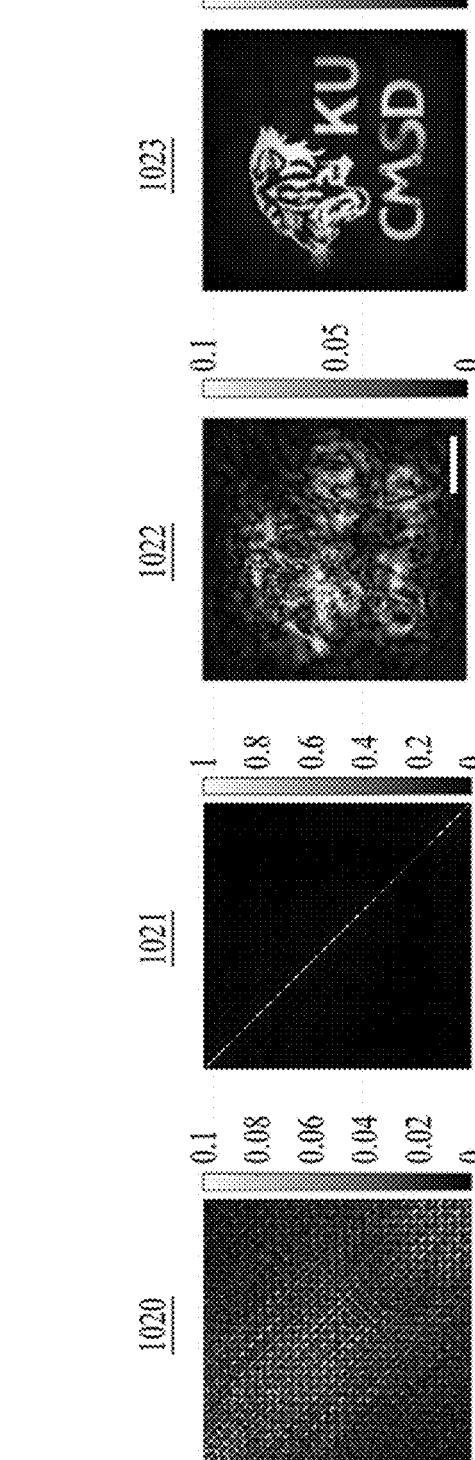
Figure 11A:
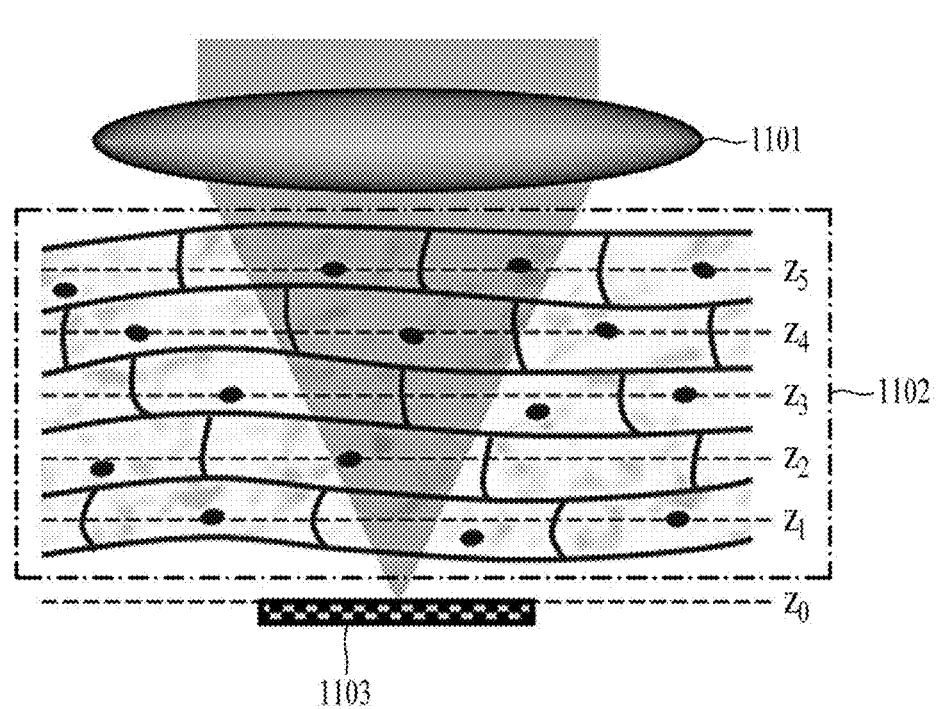
Figure 11B:
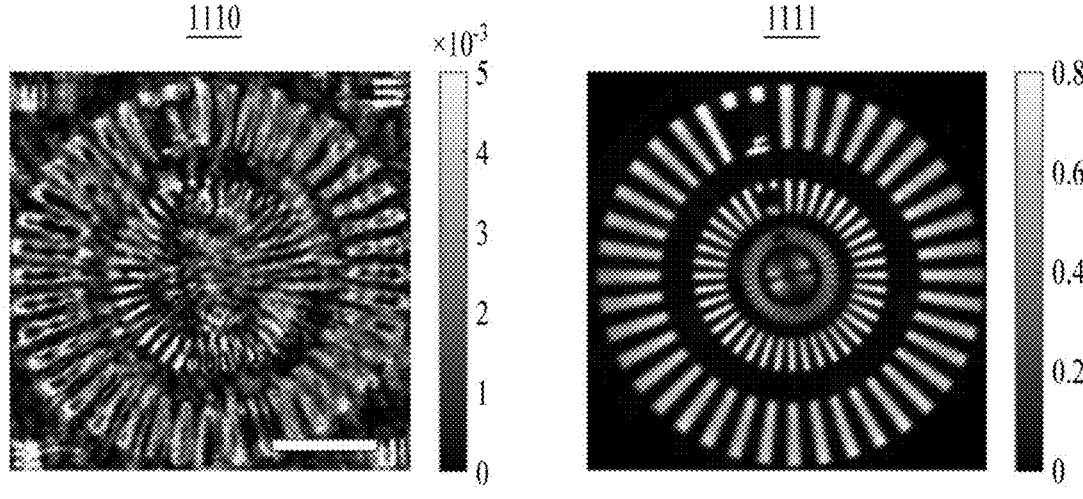
Figure 11C:
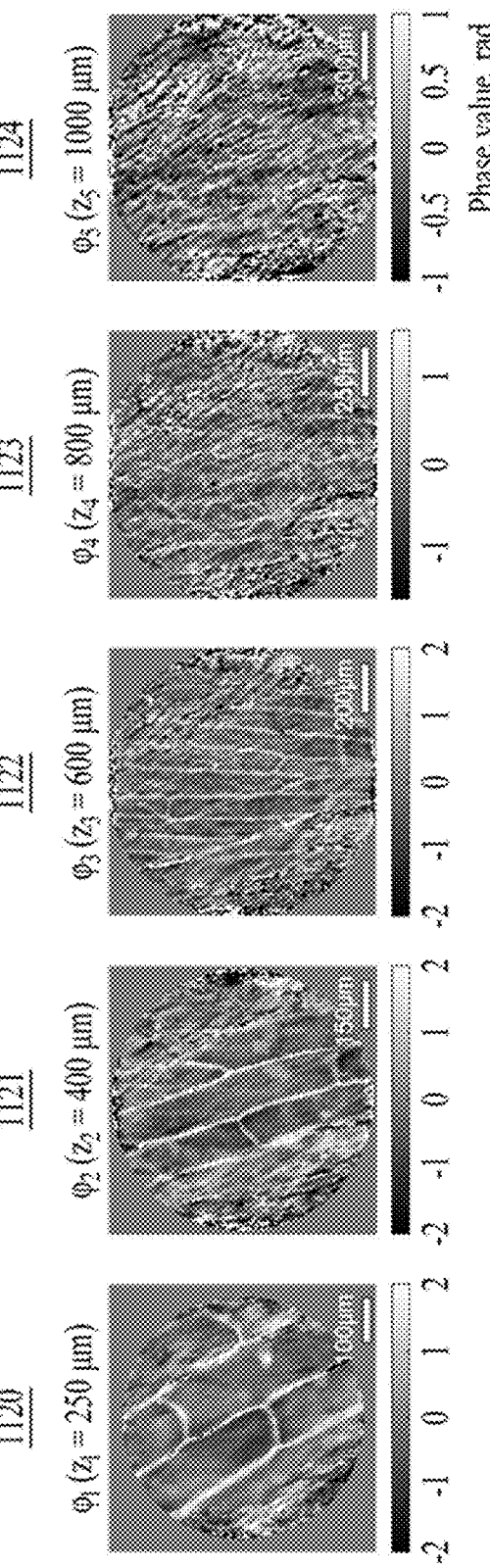

6 using the reflection matrix-based multiple scattering tracing algorithm according to an embodiment of the present disclosure;

FIGS. 10A to 10C illustrate the numerical simulation of the reflection matrix-based multiple scattering tracing algorithm according to an embodiment of the present disclosure;

FIGS. 11A to 11C illustrate an experimental proof experiment for an onion using the reflection matrix-based multiple scattering tracing algorithm according to an embodiment of the present disclosure;

FIGS. 12A to 12D illustrate an experimental proof experiment using biological tissue of the reflection matrix-based multiple scattering tracing algorithm according to an embodiment of the present disclosure;

FIGS. 13A to 13D illustrate in-vivo imaging results obtained using the reflection matrix-based multiple scattering tracing algorithm according to an embodiment of the present disclosure; and FIG. 14 illustrates the correction and restoration performance of an imaging device for correcting and reconstructing a target image in a scattering medium using the reflection matrix-based multiple scattering tracing algorithm according to an embodiment of the present disclosure.

DETAILED DESCRIPTION OF THE DISCLOSURE

Specific structural and functional descriptions of embodiments according to the concept of the present disclosure disclosed herein are merely illustrative for the purpose of explaining the embodiments according to the concept of the present disclosure. Furthermore, the embodiments according to the concept of the present disclosure can be implemented in various forms and the present disclosure is not limited to the embodiments described herein.

The embodiments according to the concept of the present disclosure may be implemented in various forms as various modifications may be made. The embodiments will be described in detail herein with reference to the drawings. However, it should be understood that the present disclosure is not limited to the embodiments according to the concept of the present disclosure, but includes changes, equivalents, or alternatives falling within the spirit and scope of the present disclosure.

The terms such as "first" and "second" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the scope of rights according to the concept of the present disclosure.

It will be understood that when an element is referred to as being "on", "connected to" or "coupled to" another element, it may be directly on, connected or coupled to the other element or intervening elements may be present. In contrast, when an element is referred to as being "directly on," "directly connected to" or "directly coupled to" another element or layer, there are no intervening elements or layers present. Other words used to describe the relationship between elements should be interpreted in a like fashion (e.g., "between," versus "directly between," "adjacent," versus "directly adjacent," etc.).

The terms used in the present specification are used to explain a specific exemplary embodiment and not to limit the present inventive concept. Thus, the expression of singularity in the present specification includes the expression of plurality unless clearly specified otherwise in context. Also, terms such as "include" or "comprise" in the specification should be construed as denoting that a certain characteristic, number, step, operation, constituent element, component or a combination thereof exists and not as excluding the existence of or a possibility of an addition of one or more other characteristics, numbers, steps, operations, constituent elements, components or combinations thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
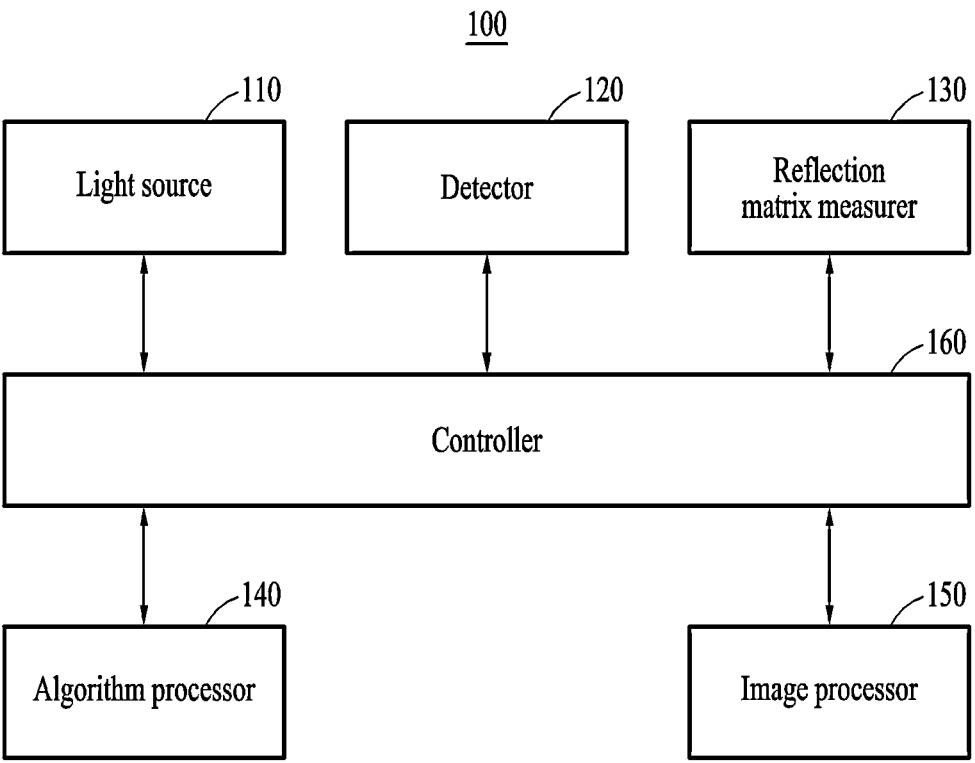
FIG. 1 illustrates an imaging device for correcting and reconstructing a target image in a scattering medium using a multiple scattering tracing algorithm based on a reflection matrix according to an embodiment of the present disclosure.

FIG. 1 illustrates an imaging device for correcting and reconstructing a target image in a scattering medium using a multiple scattering tracing algorithm based on a reflection matrix according to an embodiment of the present disclosure.

FIG. 1 illustrates components of the imaging device for correcting and reconstructing a target image in a scattering medium using the reflection matrix-based multiple scattering tracing algorithm according to an embodiment of the present disclosure.

Referring to FIG. 1, an imaging device 100 for correcting and reconstructing a target image in a scattering medium using the reflection matrix-based multiple scattering tracing algorithm according to an embodiment of the present disclosure includes a light source 110, a detector 120, a reflection matrix measurer 130, an algorithm processor 140 and an image processor 150. Here, the components of the imaging device 100 are controlled based on a controller 160. For example, the imaging device 100 traces the trajectory of multiple scattering that occurs inside a scattering medium and uses it for imaging an internal object.

For example, the imaging device 100 uses a reflection matrix-based multiple scattering tracing algorithm as an algorithm that is applied as post-processing to reflection matrix data obtained through reflection signals of a target object and a scattering medium without labeling.

The imaging device 100 may acquire a high-depth, high-resolution image, can be applied clinically, and can be used as measurement equipment because it can obtain images of the inside of samples, such as semiconductors or biological tissues, without disassembling the inside.

For example, the imaging device 100 may use a reflection matrix-based multiple scattering tracing algorithm a that is an algorithm applicable to various types of time-resolved deaxial holographic microscopes or reflection matrix microscopes.

According to an embodiment of the present disclosure, the light source 110 may be a source provider for providing a pulse laser.

For example, biological tissue that can be used as a target object is a scattering medium and can be most easily applied to image structures with a large change in refractive index due to multiple scattering components thereinside. As examples thereof, there are the central nervous system, brain nerve tissue, and blood vessels.

As approach deeper into biological tissue, the resolution decreases depending on the scattering trajectory given by the tissue structure. The imaging device 100 may correct a high-order inverse scattering problem by correcting errors due to multiple scattering trajectories inside a scattering medium that is a part where multiple scattering occurs.

For example, the scattering medium may include any medium that contains multiple scattering components capable of scattering light internally, such as biological tissue or the skull. The detector 120 according to an embodiment of the present disclosure may detect light that is returned after incident light transmits and reflects multiple scattering components of a target object.

For example, the light source 110 may inject light into the target object as a point light, and may change the incident position on the target object by changing the position of the point light.

Meanwhile, the detector 120 may detect a changed sensing pixel according to a changed incident location.

According to an embodiment of the present disclosure, the reflection matrix measurer 130 may measure a time-resolved reflection matrix that reflects multiple scattering component-based multiple scattering trajectories based on light that returns after passing through a scattering medium of the target object.

For example, the reflection matrix measurer 130 sets the matrix components as light concentrated at each position on the plane of the target object, and measures a time-resolved reflection matrix determined by the intensity and phase of the electric field measured on the output basis at each position of the camera placed on the conjugate image plane of the object surface and the resulting reflected light on the input basis.

According to an embodiment of the present disclosure, the algorithm processor 140 performs numerical iterative access to a plurality of phase planes approximated from a scattering medium according to the multiple scattering tracing algorithm to obtain an incident transmission matrix and a reflection transmission matrix, and obtains an object reflection matrix by reflecting the obtained incident transmission matrix and the inverse matrix of the obtained reflection transmission matrix into the measured time-resolved reflection matrix.

For example, a plurality of phase planes is used to find a plurality of phase plane phase maps by approximating a scattering medium to a plurality of virtual phase planes.

For example, the multiple scattering tracing algorithm may be an algorithm that finds a plurality of phase plane phase maps that can explain a measured reflection matrix by approximating the measured reflection matrix to a virtual plurality of phase planes.

In other words, the multiple scattering tracing algorithm of the present disclosure may be an algorithm for constructing a reflection matrix by measuring the intensity and phase map of light passing through a scattering medium when different illumination is incident, and then approximating the scattering medium as a virtual multiple phase plane and finding the phase map of the virtual phase plane from the measured reflection matrix.

For example, the algorithm processor 140 multiplies an input or output end of a time-resolved reflection matrix by a spatial propagation matrix $P_k$ corresponding to a distance to a k-th phase plane, based on the multiple scattering tracing algorithm to repeatedly perform numerical access to each phase plane, thereby obtaining a plurality of incident transmission matrices and reflection transmission matrices corresponding to the k-th.

For example, k-th may represent a specific number and correspond to a natural number.

For example, there may be 5 phase planes, and k may correspond to one of 1 to 5, and may be changed without being limited to the number.

The algorithm processor 140 according to an embodiment of the present disclosure may obtain a difference in phase delay values of two points in consideration of the case where light is focused on two different points for a specific phase plane among a plurality of phase planes, based on the multiple scattering tracing algorithm, and may apply the obtained difference to the incident transmission matrix and reflection transmission matrix obtained for the specific phase plane.

For example, The algorithm processor 140 may calculate an inverse matrix for each of the incident transmission matrices and reflection transmission matrices related to phase values for a plurality of points that respectively constitute a plurality of phase planes and phase planes for the multiple scattering components of the scattering medium according to the multiple scattering tracing algorithm, and may obtain an object reflection matrix for the target object by reflecting the calculated inverse matrices in the time-resolved reflection matrix.

For example, each of the plural phase planes may calculate a transmission matrix in relation to multiple scattering components inside the scattering medium, design a first phase plane based on the calculated transmission matrix, and design a second phase plane based on the inverse transmission matrix of the calculated transmission matrix on the designed first phase plane to be located virtually inside or on the scattering medium.

Figure 5:
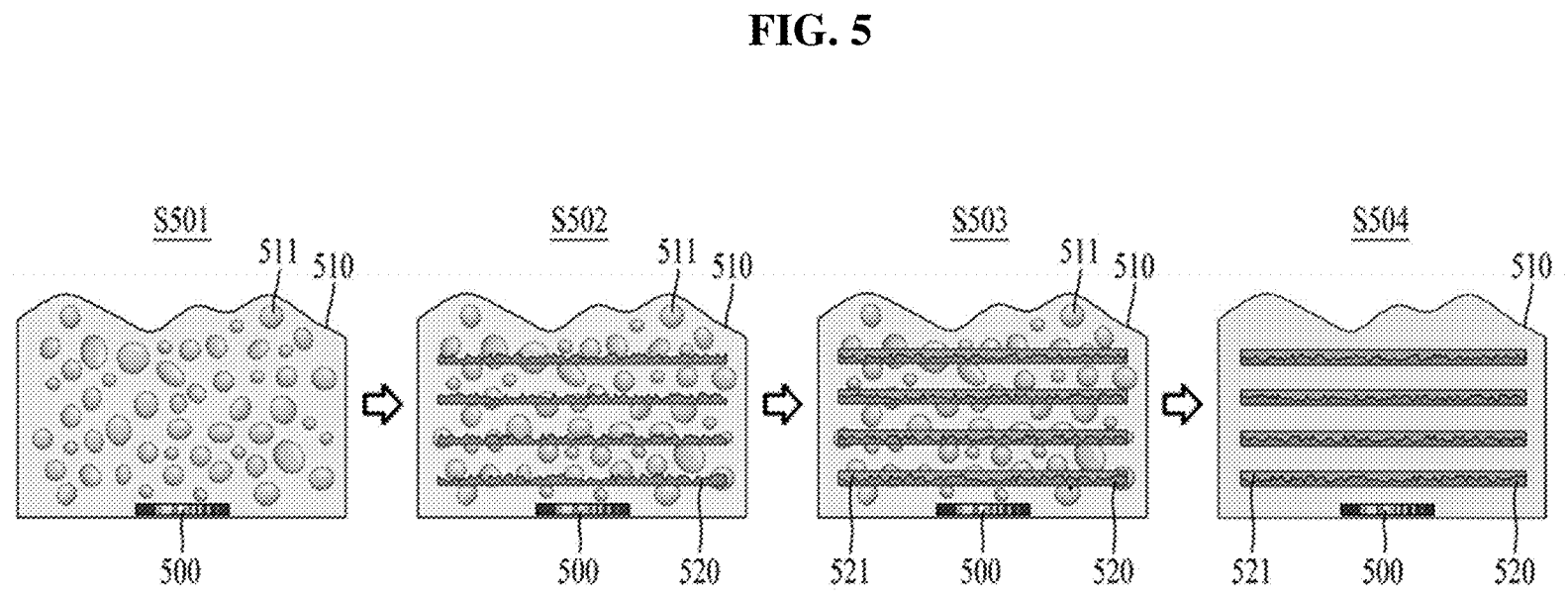

The design of the plurality of phase planes is supplementally explained using FIG. 5.

The positions of the plural phase planes may be determined as locations where the electric field intensity, obtained by measuring the electric field intensity according to the application of the multiple scattering tracing algorithm while changing the distance from the target object, is greater than a reference value.

The positioning of the plural phase planes is supplementally explained with reference to FIG. 12B.

The number of the plural phase planes may be determined by measuring the intensity of the electric field according to the application of the multiple scattering tracing algorithm while changing the number of phase planes, and by also considering a calculation time according to the changed number.

A supplementary explanation will be given using FIG. 12C regarding the determination of the number of plural phase planes.

Accordingly, the present disclosure may provide a device for tracing multiple scattering trajectories using a time-resolved reflection matrix obtained from an imaging device using a time-resolved light source, and then correcting and reconstructing an internal target image located deep inside a scattering medium such as biological tissue by correcting the traced multiple scattering trajectory; and a method thereof.

In addition, the present disclosure may obtain a time-resolved reflection matrix of the scattering medium, and then reconstruct the trajectory of multiple scattered waves using a numerical iterative technique according to the multiple scattering tracing (MST) algorithm, and reconstruct and correct a target image corresponding to an object inside a scattering medium image using the reverse process of the trajectory of the reconstructed multiple scattering waves.

Figure 2A:
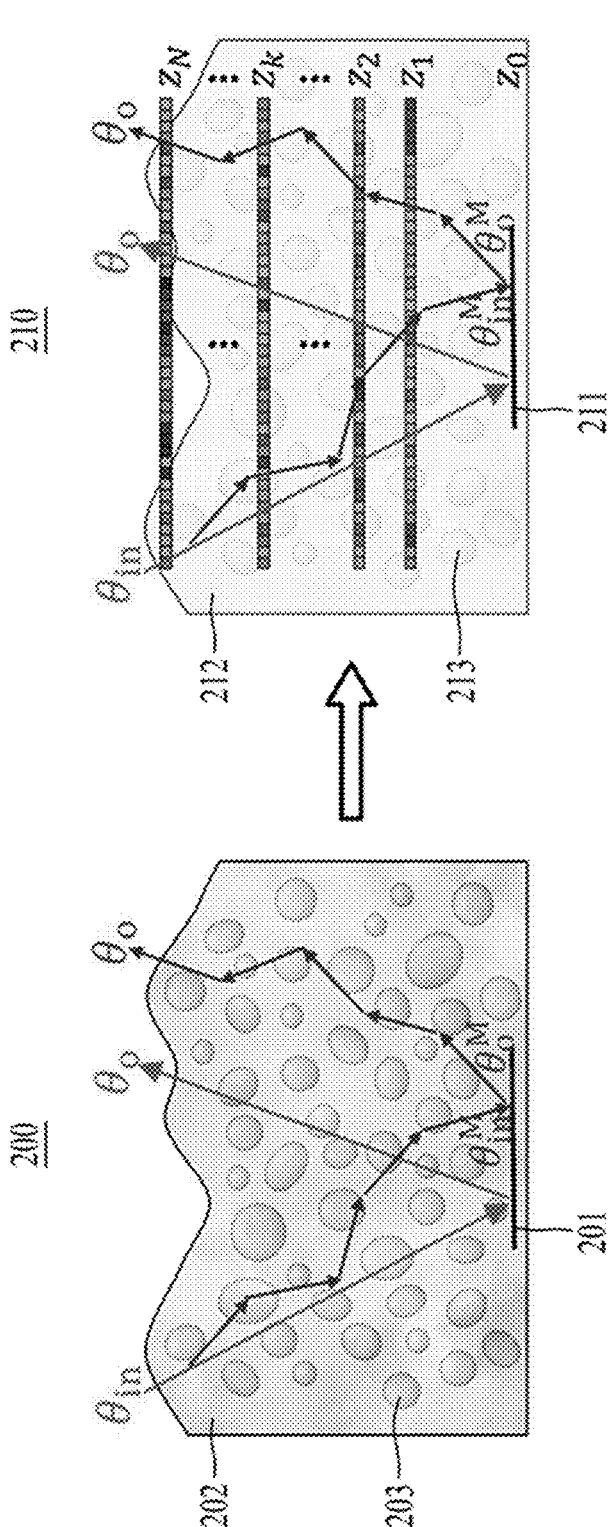
FIGS. 2A and 2B illustrate a multi-layer phase plane approximation structure of a scattering medium related to the reflection matrix-based multiple scattering tracing algorithm according to an embodiment of the present disclosure.
Figure 2B:
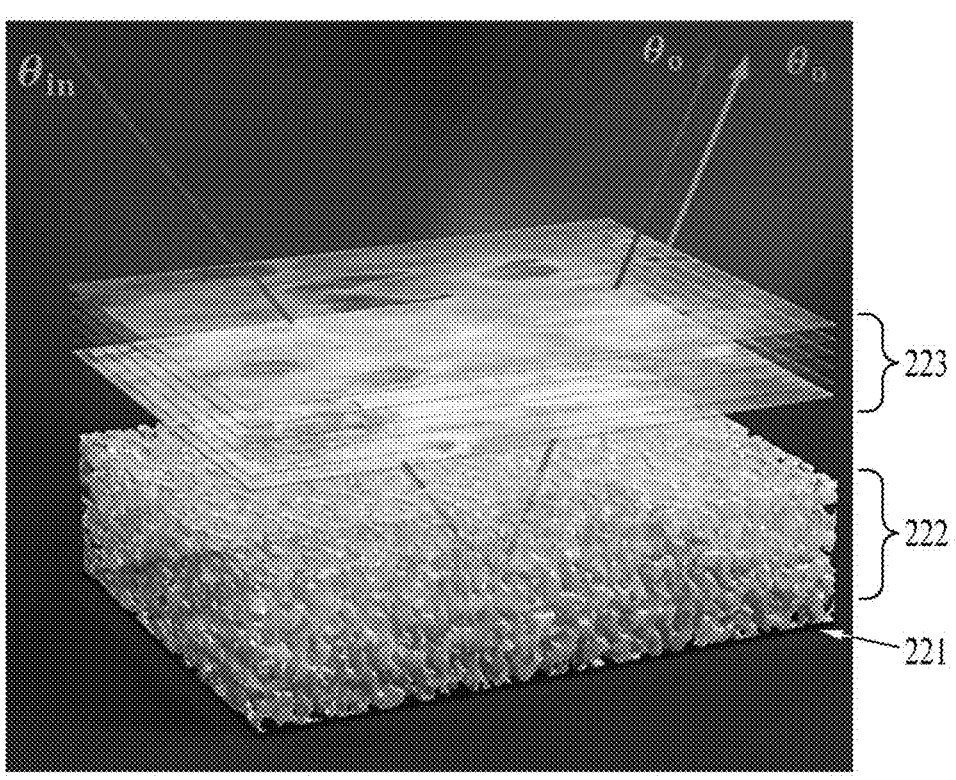

FIGS. 2A and 2B illustrate a multi-layer phase plane approximation structure of a scattering medium related to the reflection matrix-based multiple scattering tracing algorithm according to an embodiment of the present disclosure.

FIG. 2A illustrates a multi-layer phase plane approximation structure for solving a scattering distortion problem due to the multiple scattering type of a scattering medium in relation to the multi-layer phase plane approximation structure of the scattering medium related to the reflection matrix-based multiple scattering tracing algorithm according to an embodiment of the present disclosure.

Referring to FIG. 2A illustrating a schematic diagram 200 of a conventional structure that has a scattering distortion problem depending on the multiple scattering type of a scattering medium, multiple scattering distortion problems due to multiple scattering components 203 occur in a process ($\theta_{in}$) where light passes through a scattering medium 202 and is incident on a target object 201 and a process ($\theta_o$) where the light is reflected and returned, and this distortion is not taken into account by scattering input ($\theta^M_{in}$) and scattering output ($\theta^M_o$).

This problem should be solved by approximating the scattering medium 202 as a set of multi-layered phase planes to address a high-order inverse scattering problem.

In a schematic diagram 210 having a multi-layer phase plane approximation structure according to an embodiment of the present disclosure, multiple scattering distortion problems occur due to the multiple scattering components 203 in the process ($\theta_{in}$) where light passes through a scattering medium 212 and is incident on a target object 211 and in the process ($\theta_o$) where the light is reflected and returned, and this distortion is approximated by a plurality of phase planes ($Z_1$ to $Z_N$) for scattering input ($\theta^M_{in}$) and scattering output ($\theta^M_o$) to simplify the high-order inverse scattering problem by finding the phase value of each phase plane.

In other words, the imaging device according to an embodiment of the present disclosure minimizes scattering caused by the multiple scattering components 213 with a plurality of phase planes in the scattering medium 212, thereby correcting the distortion caused by the multiple scattering components 213 of the scattering medium 212 in a process ($\theta_{in}$) where the distortion of scattering input ($\theta^M_{in}$) and scattering output ($\theta^M_o$) is corrected and light is incident and a process ($\theta_o$) where the light is reflected and returned.

In relation to a multi-layer phase plane approximation structure of a scattering medium related to the reflection matrix-based multiple scattering tracing algorithm according to an embodiment of the present disclosure, FIG. 2B three-dimensionalizes and illustrates the multi-layer phase plane approximation structure to solve a scattering distortion problem due to the multiple scattering type of the scattering medium.

Referring to FIG. 2B, a three-dimensional diagram 220 of the multi-layer phase plane approximation structure according to an embodiment of the present disclosure may have a structure where a target object 221 is located inside or under a scattering medium 222 and a multi-layer phase plane 223 is applied.

The three-dimensional diagram 220 with the multi-layer phase plane approximation structure according to an embodiment of the present disclosure illustrates a form in which an imaging device corrects the distortion caused by multiple scattering by the scattering medium 222 through the multi-layer phase plane 223 when optically imaging the target object 221.

For example, the multi-layer phase plane may be a configuration to obtain a phase value for correcting virtually designed scattering distortion, or may be an actual phase filter.

Figure 3:
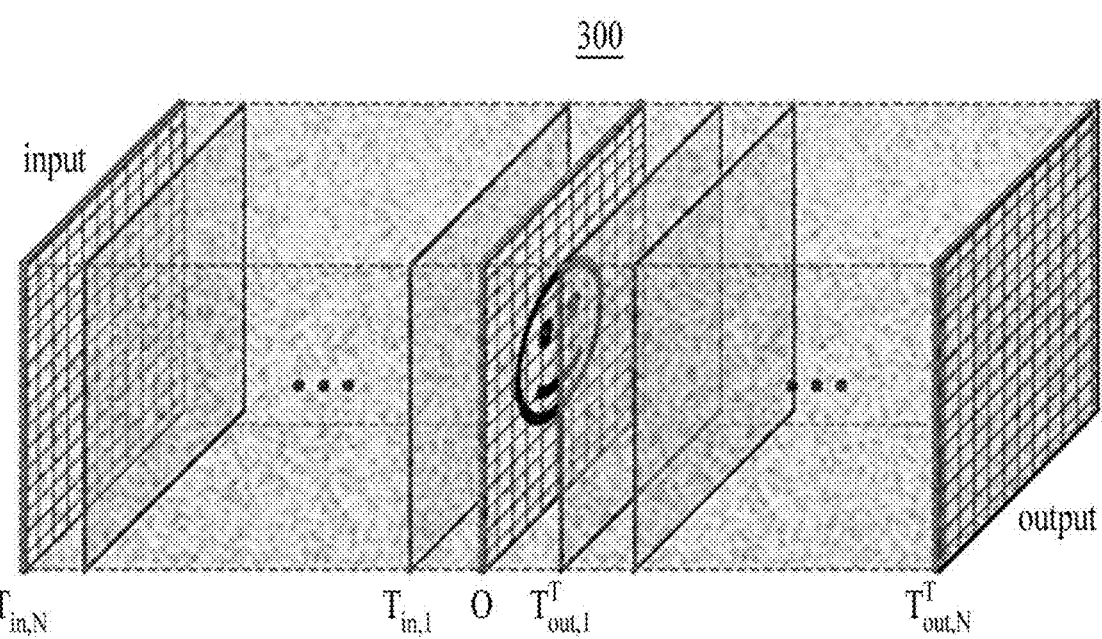
FIG. 3 illustrates a reflection matrix structure by a multi-layer phase plane approximation model related to the reflection matrix-based multiple scattering tracing algorithm according to an embodiment of the present disclosure.

FIG. 3 illustrates a reflection matrix structure by a multi-layer phase plane approximation model related to the reflection matrix-based multiple scattering tracing algorithm according to an embodiment of the present disclosure.

FIG. 3 exemplifies a reflection matrix structure by the multi-layer phase plane approximation model related to the reflection matrix-based multiple scattering tracing algorithm according to an embodiment of the present disclosure.

FIG. 3 shows approximations of incident transmission matrix, reflection transmission matrix and object reflection matrix in a reflection matrix structure 300 according to an embodiment of the present disclosure.

As an example for understanding the reflection matrix structure 300, an object O is located in the center, and phase planes reflecting incidence and reflection are located on both sides, but the object O is located inside or below a scattering medium, and a plurality of phase planes are located inside the scattering medium, so reflections occur in the same space.

Regarding the reflection matrix structure 300, a time-resolved reflection matrix R may be approximated as the matrix product of the transmission matrices of respective phase planes and an object reflection matrix corresponding to a reflection matrix of an object to be imaged.

Equation 1 below may be used to approximate an object reflection matrix:

$$R \approx T_{out,N}^T \ \cdots \ T_{out,1}^T O T_{in,1} \ \cdots \ T_{in,N} = T_{out}^T O T_{in} \qquad \text{[Equation 1]}$$

In Equation 1, R represents a time-resolved reflection matrix, $T_{in}$ represents an incident transmission matrix, $T_{out}^T$ represents a reflection transmission matrix, and O represents an object reflection matrix.

The incident transmission matrix may represent a transmission matrix in an incident process from the surface of a scattering medium to the depth where an object to be imaged is located.

The reflection transmission matrix may correspond to the transmission matrix of a process in which light is reflected and returned.

Figure 4:
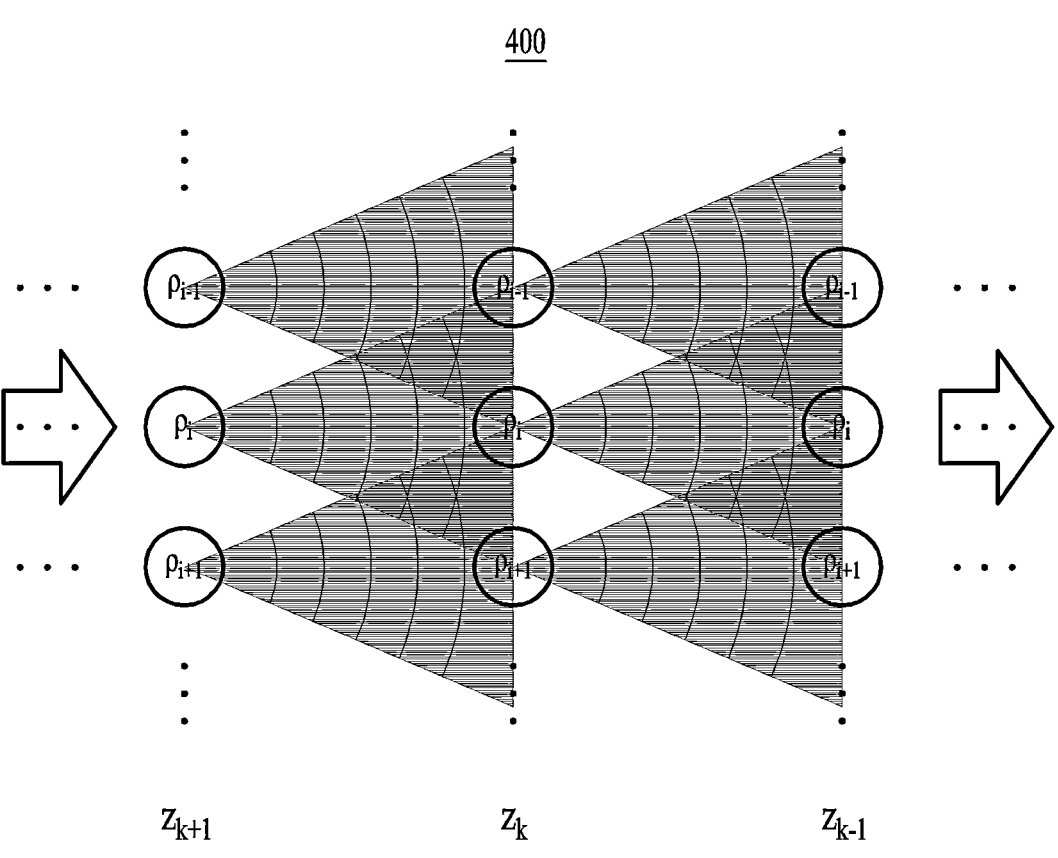
FIG. 4 illustrates a transmission matrix model structure of each phase plane related to the reflection matrix-based multiple scattering tracing algorithm according to an embodiment of the present disclosure.

FIG. 4 illustrates a transmission matrix model structure of each phase plane related to the reflection matrix-based multiple scattering tracing algorithm according to an embodiment of the present disclosure.

FIG. 4 exemplifies a transmission matrix model structure of each phase plane related to the reflection matrix-based multiple scattering tracing algorithm according to an embodiment of the present disclosure.

In a transmission matrix model structure 400 of each phase plane related to the reflection matrix-based multiple scattering tracing algorithm according to an embodiment of the present disclosure of FIG. 4, the transmission matrix $T_k$ of each phase plane passing through a phase plane $Z_k$, a phase plane $Z_{k+1}$ and a phase plane $Z_{k-1}$ is determined as the product of a phase delay value of a space inside each plane and a spatial propagation matrix.

For example, the spatial propagation matrix may be expressed as a spatial propagation matrix ($P_{k-1, k}$) of the k-th phase plane to the k−1th phase plane.

For example, the transfer function of each phase plane may be utilized in relation to the phase delay value.

FIG. 5 illustrates a process for designing a plurality of phase planes related to a multiple scattering tracing algorithm based on a reflection matrix in an imaging method according to an embodiment of the present disclosure.

FIG. 5 exemplifies a process for designing a plurality of phase planes related to a multiple scattering tracing algorithm based on a reflection matrix in the imaging method according to an embodiment of the present disclosure.

Referring to FIG. 5, the imaging method according to an embodiment of the present disclosure determines a target object 500 located inside or under the scattering medium 510 in step S501.

Multiple scattering components 511 are included inside the scattering medium 510.

In step S502 of the imaging method according to an embodiment of the present disclosure, a first phase plane 520 is configured based on a transmission matrix T in relation to the design of a plurality of phase planes inside the scattering medium 510.

In step S503 of the imaging method according to an embodiment of the present disclosure, a second phase plane 521 is constituted based on inverse transmission matrix T−1 in relation to the design of a plurality of phase planes inside the scattering medium 510.

In step S504 of the imaging method according to an embodiment of the present disclosure, an image for the target object 500 is acquired in a state where the multiple scattering components 511 inside the scattering medium 510 are removed.

The first phase plane 520 and second phase plane 521 according to an embodiment of the present disclosure are combined to form one phase plane.

Figure 6:
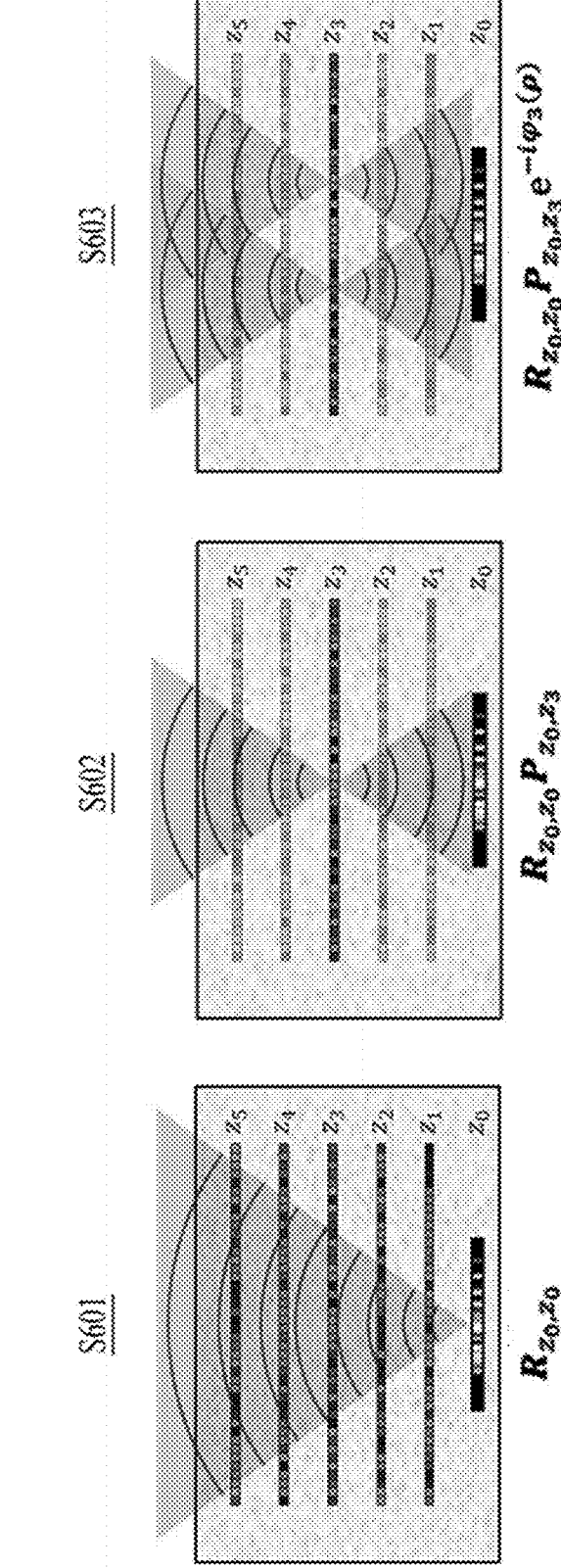
FIGS. 6 and 7 illustrate a numerical iterative model structure and numerical iterative process related to the reflection matrix-based multiple scattering tracing algorithm according to an embodiment of the present disclosure.
Figure 7:
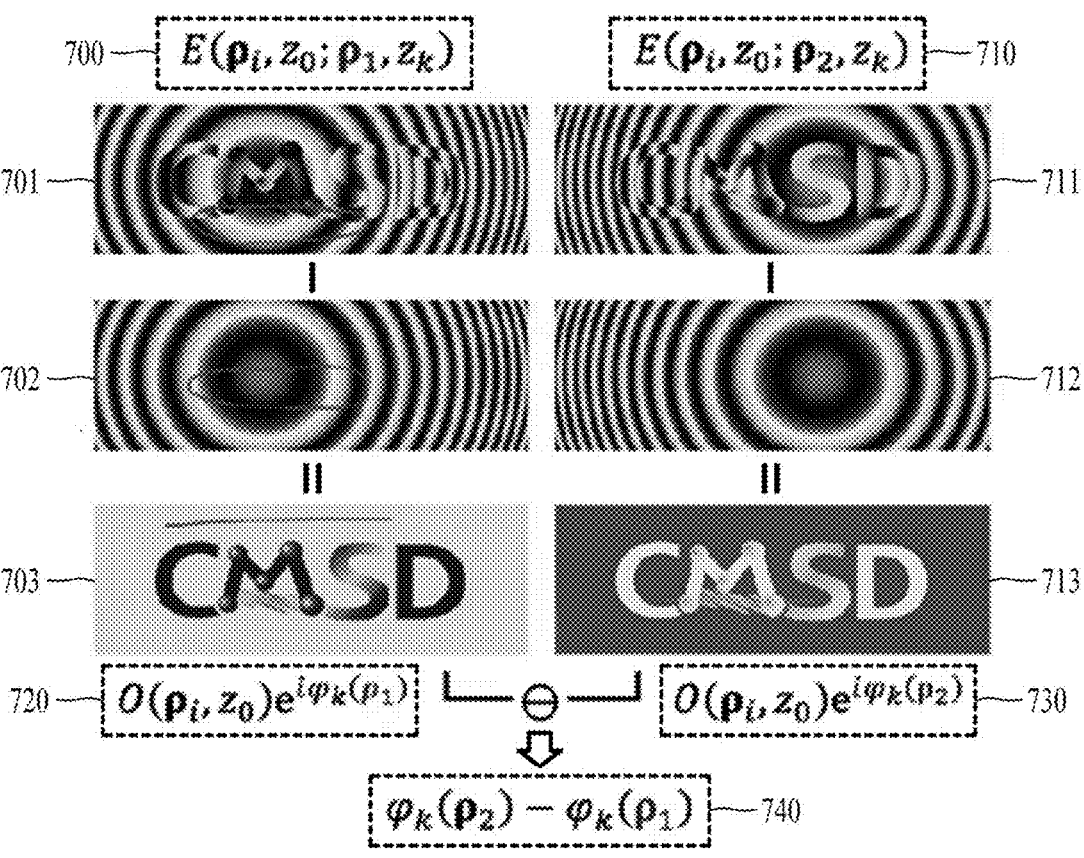

FIGS. 6 and 7 illustrate a numerical iterative model structure and numerical iterative process related to the reflection matrix-based multiple scattering tracing algorithm according to an embodiment of the present disclosure.

FIG. 6 exemplifies a numerical iterative model structure and numerical iterative process related to the multiple scattering tracing algorithm based on the reflection matrix in the imaging method according to an embodiment of the present disclosure.

To obtain image information of an object inside a scattering medium by the imaging method according to an embodiment of the present disclosure, an object inside a scattering medium, a reflection matrix of the object is obtained by solving the inverse scattering problem of Equation 1.

Accordingly, in relation to the multiple scattering tracing algorithm based on the reflection matrix in the imaging method, Equation 1 may correspond to a (2N+1)-order high-order inverse scattering problem when passing through 2N planes during the incident and reflection process and including a reflection surface if the number of phase planes is N.

To solve the above-mentioned problem, the imaging method includes performing a numerical iterative model structure and numerical iterative process related to the multiple scattering tracing algorithm based on the reflection matrix.

Referring to FIG. 6, in step S601 of the imaging method according to an embodiment of the present disclosure, an initial optical reflection matrix in the input/output structure of an initial reflection matrix is measured.

Examining step S601 of the imaging method, each matrix component of the measured time-resolved reflection matrix R provides concentrated illumination at each position on an object surface, and a resulting reflected light on the input basis is determined as the intensity and phase of the electric field measured on the output basis at each position of a camera placed on the conjugate image plane of the object surface.

In step S601 of the imaging method, a time-resolved reflection matrix ($R_{zo,zo}$) is obtained.

For example, the time-resolved reflection matrix determines the input (incident) and output (reflection) for the plane ($z_o$) corresponding to the target object.

In step S602 of the imaging method according to an embodiment of the present disclosure, the phase plane is accessed in the input/output structure when a specific phase plane is accessed.

In addition, the imaging method may access each phase plane by multiplying the input or output end of the reflection matrix by a spatial propagation matrix ($P_k$) corresponding to a distance to the k-th phase plane based on the multiple scattering tracing algorithm.

In the spatial propagation matrix, an input (incident) is determined for the plane ($z_o$) corresponding to the target object, and a phase plane ($z_3$), which is an access target, is determined as an output (reflection).

As a result, the obtained matrix may be used to reconstruct the reflected image of the object by illumination (light) focused on each position of a specific phase plane.

Since the focusing surface of the illumination is away from the object's surface, the wavefront of the light illuminated on the object may correspond to the form of a spherical wave.

In step S603 of the imaging method according to an embodiment of the present disclosure, phase shift is acquired and corrected in the input/output structure according to the method of acquiring the phase map of the corresponding phase plane by correlation.

When reconstructed images of the object illuminated by first and second spherical waves in consideration of the case of focusing on two different points of the corresponding phase plane in step S603 of the imaging method according to an embodiment of the present disclosure, the two images may have a correlation based on common object image information in the overlapping area as shown in the drawing.

Here, the phase value of the correlation value corresponds to a difference between the phase delay values of two points on the phase plane.

When this process is repeated at all locations of the phase plane, the phase delay map of the phase plane may be found.

The spatial propagation matrix reflecting the difference in the phase delay values may be obtained using Equation 2 below:

$$P_{z_i,z_j}(\rho_i; \rho_2) = \frac{1}{i\lambda} \frac{(z_i - z_j)\exp\left(in_0 k_0 \sqrt{|\rho_i - \rho_j|^2 + (z_i - z_j)^2}\right)}{|\rho_i - \rho_j|^2 + (z_i - z_j)^2} \quad \text{[Equation 2]}$$

In Equation 2, P represents a spatial propagation matrix, p represents a phase value at a specific location of a phase plane, z represents the phase plane, and i and j represent natural numbers.

When this process is performed numerically and repeatedly for 2N planes in the incident and reflection process, the transmission matrix ($T_{in}$) in the incident process of a scattering medium in Equation 1 and the transmission matrix ($T_{out}$) in the reflection process thereof may be obtained. By multiplying both sides of the reflection matrix by the inverse matrix of the finally obtained transmission matrix, an object reflection matrix may be obtained as shown in Equation 3 below:

$$O = \left(T_{out}^T\right)^{-1} R (T_{in})^{-1} \quad \text{[Equation 3]}$$

In Equation 2, R represents a time-resolved reflection matrix, $T_{in}$ represents an incident transmission matrix, $T^T_{out}$ represents a reflection transmission matrix, and O represents an object reflection matrix.

According to an embodiment of the present disclosure, the imaging method may obtain the image of a final object through the reflection matrix of the obtained object.

FIG. 7 supplementally explains the numerical iterative model structure and numerical iterative process of step S603 of FIG. 6 related to the multiple scattering tracing algorithm based on the reflection matrix in the imaging method according to an embodiment of the present disclosure FIG. 7 illustrates an electric field image function 700 and an electric field image function 710. With regard to the electric field image function 700 and the electric field image function 710. An object reflection matrix 720 and an object reflection matrix 730 are obtained based on the reflection matrix-based multiple scattering tracing algorithm, and a phase value of a correlation value between the object reflection matrix 720 and the object reflection matrix 730 derives a difference 740 between phase delay values of two points on the phase plane.

The electric field image function 700 may be related to a first point on the phase plane, and the electric field image function 710 may be related to a second point on the phase plane.

An image 701 based on the electric field image function 700 includes a target object image and multiple scattering.

An image 711 based on the electric field image function 710 includes a target object image and multiple scattering.

The image 701 and the image 711 show a difference in resolution depending on a difference between the first point and the second point.

The difference in resolution may be considered as a difference according to the phase delay values of two points on the phase plane.

A target object image 703 is obtained by excluding an image 702 from the image 701, and a target object image 713 is obtained by excluding an image 712 from the image 711.

A difference 740 may correspond to a difference reflecting the phase value of each position in a transfer function for a k-th phase plane.

Figure 8:
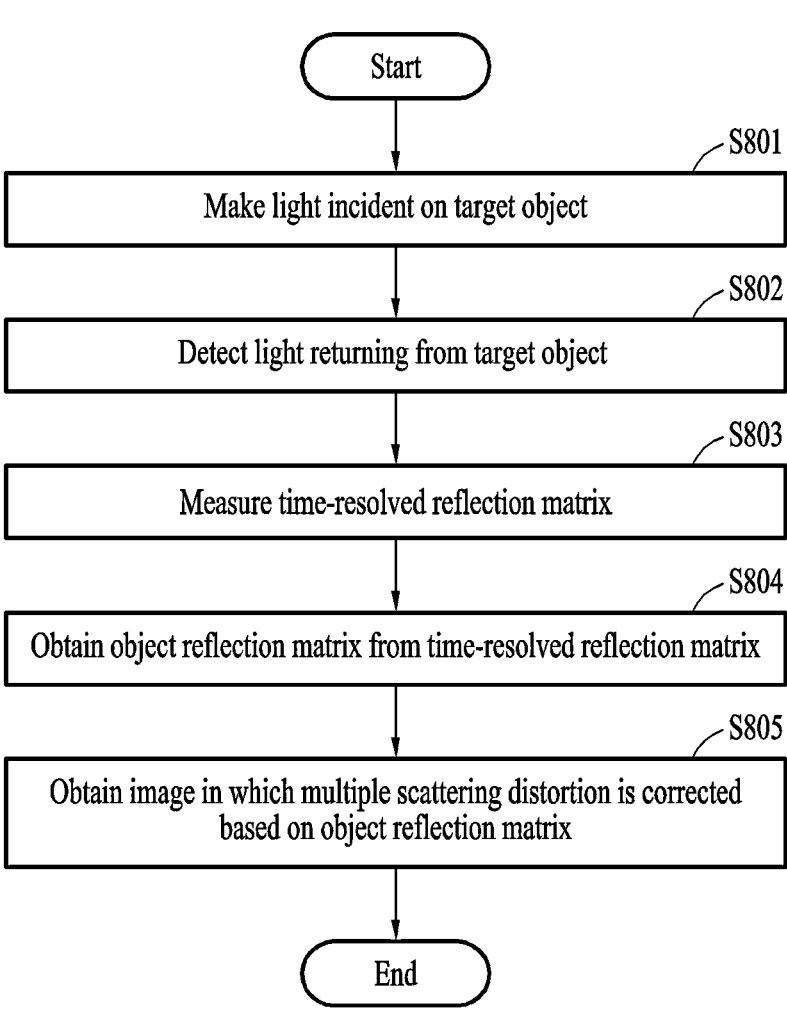
FIGS. 8 and 9 illustrate an imaging method of correcting and reconstructing a target image in a scattering medium
Figure 9:
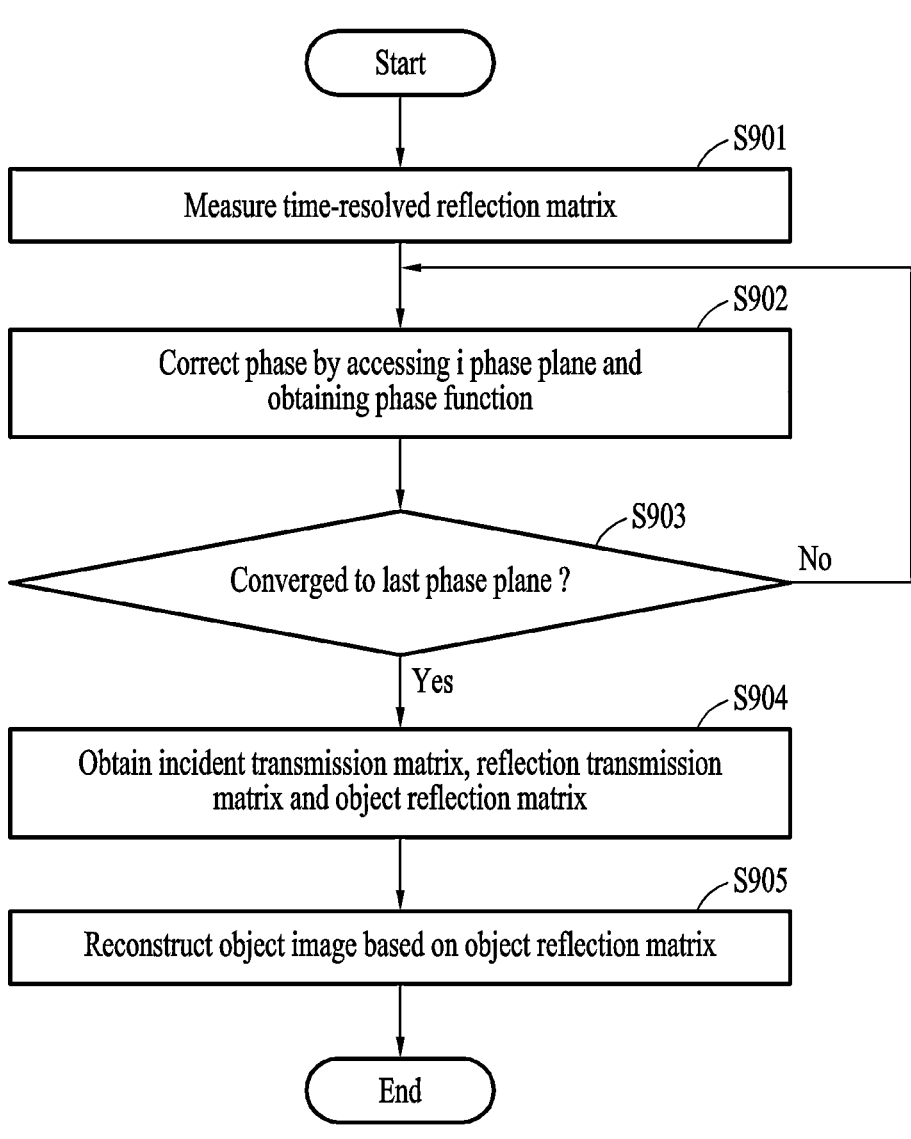

FIGS. 8 and 9 illustrate an imaging method of correcting and reconstructing a target image in a scattering medium using the reflection matrix-based multiple scattering tracing algorithm according to an embodiment of the present disclosure.

FIG. 8 exemplifies a procedure of tracing multiple scattering trajectories from a time-resolved reflection matrix and then correcting them to obtain an image of a target such as biological tissue located deep inside the scattering medium in the imaging method of correcting and reconstructing a target image in a scattering medium using the reflection matrix-based multiple scattering tracing algorithm according to an embodiment of the present disclosure.

Hereinafter, the imaging method of correcting and reconstructing a target image in a scattering medium using the reflection matrix-based multiple scattering tracing algorithm according to an embodiment of the present disclosure is described as the imaging method for convenience of explanation.

Referring to FIG. 8, in step S801 of the imaging method according to an embodiment of the present disclosure, light is incident on a target object.

That is, in the imaging method according to an embodiment of the present disclosure, light is incident on an object by passing through a scattering medium and multiple scattering components within the scattering medium.

In step S802 of the imaging method according to an embodiment of the present disclosure, light returning from the target object is detected.

That is, the imaging method according to an embodiment of the present disclosure, incident light detects light that is returned after the incident light passes through and reflects multiple scattering components from the target object.

In step S803 of the imaging method according to an embodiment of the present disclosure, a time-resolved reflection matrix is measured.

That is, the imaging method according to an embodiment of the present disclosure measures a time-resolved reflection matrix reflecting multiple scattering trajectories based on multiple scattering components based on the returning light.

In step S804 of the imaging method according to an embodiment of the present disclosure, an object reflection matrix is obtained from the time-resolved reflection matrix.

That is, the imaging method according to an embodiment of the present disclosure may perform numerical iterative access to a plurality of phase planes to obtain an incident transmission matrix and a reflection transmission matrix, and reflect the inverse matrices of the obtained incident transmission matrix and obtained reflection transmission matrix in the time-resolved reflection matrix to obtain an object reflection matrix.

In step S805 of the imaging method according to an embodiment of the present disclosure, an image in which multiple scattering distortion is corrected is obtained based on the object reflection matrix.

That is, the imaging method according to an embodiment of the present disclosure acquires an image for the target object in the image in which multiple scattering distortion is corrected according to the multiple scattering trajectory based on the object reflection matrix.

FIG. 9 exemplifies a procedure of performing a multiple scattering tracing algorithm by the imaging method of correcting and reconstructing a target image in a scattering medium using the reflection matrix-based multiple scattering tracing algorithm according to an embodiment of the present disclosure.

For convenience of explanation, the imaging method of correcting and reconstructing a target image in a scattering medium using the reflection matrix-based multiple scattering tracing algorithm according to an embodiment of the present disclosure is described as the imaging method.

Referring to FIG. 9, a time-resolved reflection matrix is measured in step S901 of the imaging method according to an embodiment of the present disclosure.

That is, the imaging method according to an embodiment of the present disclosure measures a time-resolved reflection matrix reflecting the multiple scattering components-based multiple scattering trajectory based on returning light.

In step S902 of the imaging method according to an embodiment of the present disclosure, the phase is corrected by accessing the i phase plane and obtaining the phase function.

In step S903 of the imaging method according to an embodiment of the present disclosure, it is determined whether it converges to the last phase plane.

That is, in the imaging method according to an embodiment of the present disclosure, step S904 is performed when the approach and phase correction to the last phase plane are completed, and the process returns to step S902 when it is not the last phase plane.

In step S904 of the imaging method according to an embodiment of the present disclosure, an incident transmission matrix, a reflection transmission matrix and an object reflection matrix are obtained.

That is, the imaging method according to an embodiment of the present disclosure may perform numerical iterative access to a plurality of phase planes approximated from the scattering medium to obtain an incident transmission matrix and a reflection transmission matrix, and reflect the inverse matrices of the obtained incident transmission matrix and obtained reflection transmission matrix in the time-resolved reflection matrix to obtain an object reflection matrix.

In step S905 of the imaging method according to an embodiment of the present disclosure, the object image is reconstructed based on the object reflection matrix.

That is, the imaging method according to an embodiment of the present disclosure reconstructs and acquires an image for the target object in the image in which multiple scattering distortion is corrected according to the multiple scattering trajectory based on the object reflection matrix.

FIGS. 10A to 10C illustrate the numerical simulation of the reflection matrix-based multiple scattering tracing algorithm according to an embodiment of the present disclosure.

FIGS. 10A to 10C illustrate schematic diagrams and results related to the numerical simulation of the reflection matrix-based multiple scattering tracing algorithm according to an embodiment of the present disclosure.

FIG. 10A illustrates a schematic diagram of a simulation model related to the numerical simulation of the reflection matrix-based multiple scattering tracing algorithm according to an embodiment of the present disclosure.

Referring to a schematic diagram 1000 of FIG. 10A, a resolution target object 1001 is placed under a scattering medium 1002, and a reflection matrix is measured based on light passing through the scattering medium 1002, incident on the target object 1001, and reflected.

In the scattering medium 1002, an initial scattering medium consisting of four phase planes and a reflection matrix by the target object are constructed through numerical simulation. Here, numerical simulation involves the phase plane design illustrated in FIG. 5.

FIG. 10b illustrates the phase map and restoration results of the phase plane applied to the simulation model in relation to the numerical simulation of the reflection matrix-based multiple scattering tracing algorithm according to an embodiment of the present disclosure.

FIG. 10b illustrates a simulation phase map 1010 applied to numerical simulation and a reconstructed phase map 1011 obtained by reconstructing the simulation phase map 1010 using the multiple scattering tracing algorithm.

By comparing the simulation phase map 1010 and the reconstructed phase map 1011, it can be seen that most of the shape of the initial phase map can be reconstructed by applying the multiple scattering tracing algorithm to the reflection matrix to reconstruct the phase map of each phase plane.

FIG. 10C illustrates an application result of the multiple scattering tracing algorithm in relation to the numerical simulation of the reflection matrix-based multiple scattering tracing algorithm according to an embodiment of the present disclosure.

Referring to FIG. 10C, an image 1020 shows an image based on an initial reflection matrix R obtained by numerical simulation, an image 1021 shows an image of a reconstructed target object reflection matrix, an image 1022 shows a confocal image of an initial object distorted by an initial scattering medium, and an image 1023 shows an image of an object reconstructed by the multiple scattering tracing algorithm.

In the initial reflection matrix, strong signal intensity is distributed in an off-diagonal component due to the scattering medium.

However, in the case of a reconstruction through the multiple scattering tracing algorithm, most of the multiple scattering is removed and signals are distributed only in a diagonal component. In addition, it can be seen in the images 1022 and 1023 that the image distorted by multiple scattering is properly reconstructed after applying the multiple scattering tracking algorithm.

FIGS. 11A to 11C illustrate an experimental proof experiment for an onion using the reflection matrix-based multiple scattering tracing algorithm according to an embodiment of the present disclosure.

FIGS. 11A to 11C illustrate a schematic diagram and result related to an experimental proof experiment for an onion using the reflection matrix-based multiple scattering tracing algorithm according to an embodiment of the present disclosure.

FIG. 11A illustrates a schematic diagram of a multi-layered onion tissue used as a scattering medium and a resolution object placed under the onion tissue, in relation to the experimental proof experiment for an onion using the reflection matrix-based multiple scattering tracing algorithm according to an embodiment of the present disclosure.

Referring to a schematic diagram 1100 of FIG. 11A, a resolution target object 1101 is placed under a thick onion tissue 1102 with a multi-layer structure, and a reflection matrix is measured based on light incident and reflected through an objective lens 1103.

The schematic diagram 1100 shows the experimental environment for imaging the resolution target object 1101 of the Siemens star pattern with the thick onion tissue 1102.

Here, the onion tissue 1102, used as a scattering medium, consists of 5 cell layers and has a total thickness of about 1 mm.

FIG. 11b illustrates an image reconstructed by applying the multiple scattering tracing algorithm and a confocal image without applying it in relation to the experimental proof experiment for an onion using the reflection matrix-based multiple scattering tracing algorithm according to an embodiment of the present disclosure.

Referring to FIG. 11b, a confocal image 1120 is a confocal image of an object reconstructed from the reflection matrix of the sample and may represent an image to which the multiple scattering tracing algorithm is not applied.

Meanwhile, a reconstructed image 1121 may represent an image of a reconstructed target object by the multiple scattering tracing algorithm according to an embodiment of the present disclosure.

It can be seen from the confocal image 1120 that the image of the object was severely distorted due to multiple scattering and aberration of the onion tissue.

On the other hand, the reconstructed image 1121 shows that the image of the target object has been properly restored based on the multiple scattering tracking algorithm.

FIG. 11C illustrates an image reconstructed by applying the multiple scattering tracing algorithm in relation to the experimental proof experiment for an onion using the reflection matrix-based multiple scattering tracing algorithm according to an embodiment of the present disclosure.

Referring to FIG. 11C, to apply the reflection matrix-based multiple scattering tracing algorithm according to an embodiment of the present disclosure a phase plane was assumed at 250 μm, 400 μm, 600 μm, 800 μm, and 1000 μm away from the resolution target object, and a phase map of each of the reconstructed planes was reconstructed.

A first phase plane 1120 has a distance of 250 μm, a second phase plane 1121 has a distance of 400 μm, a third phase plane 1122 has a distance of 600 μm, a fourth phase plane 1123 has a distance of 800 μm, and a fifth phase plane 1124 has a distance of 1000 μm.

The phase maps of the three phase planes close to the resolution target clearly show the onion cell image of each layer.

This proves that the phase plane reconstructed by the multiple scattering tracing algorithm properly reflects the actual structure of an onion tissue.

In the case of the fourth phase plane 1123 and the fifth phase plane 1124, the shape of the onion cell layer cannot be properly confirmed, which may be because the phase reconstruction resolution of the layer was insufficient to image onion cells.

FIGS. 12A to 12D illustrate an experimental proof experiment using biological tissue of the reflection matrix-based multiple scattering tracing algorithm according to an embodiment of the present disclosure.

FIGS. 12A to 12D illustrate a schematic diagram and results in relation to the experimental proof experiment using biological tissue of the reflection matrix-based multiple scattering tracing algorithm according to an embodiment of the present disclosure, and demonstrate the feasibility of implementing the multiple scattering tracking algorithm in general biological tissue rather than a multi-layer structure.

Figure 12A:
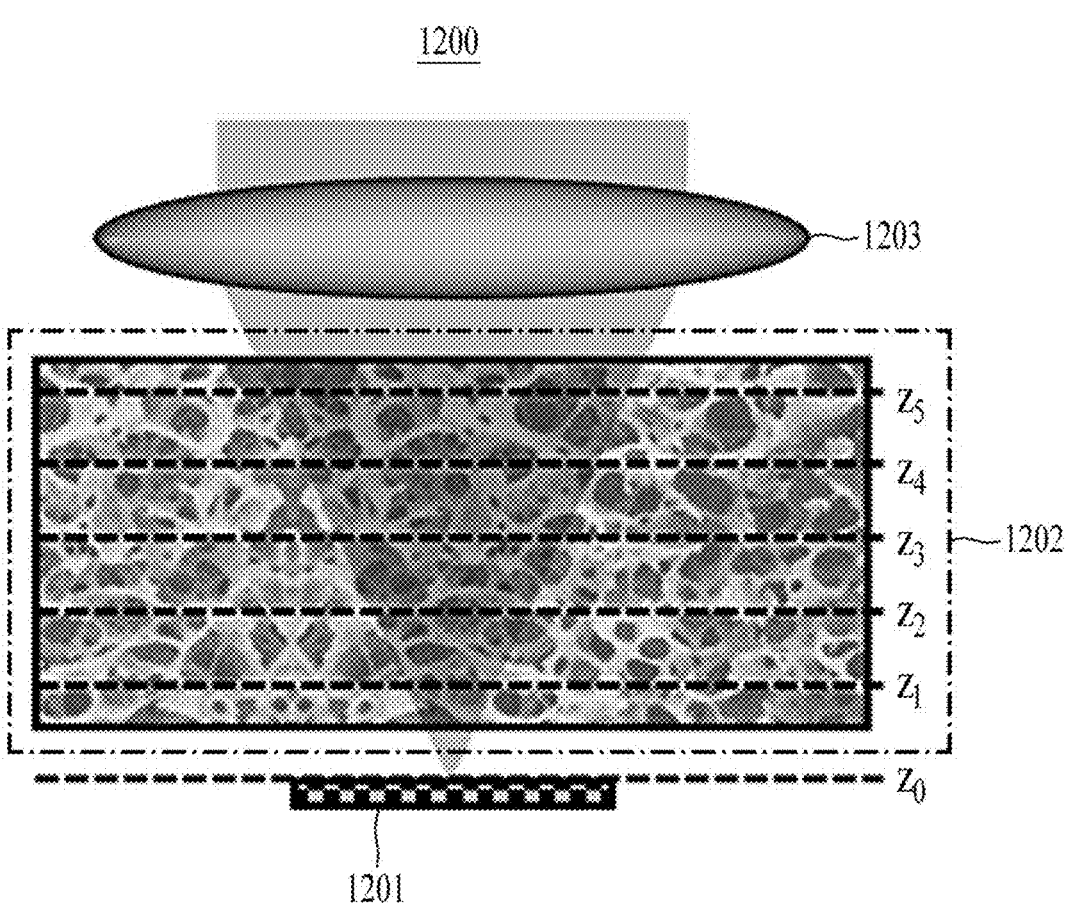

FIG. 12A illustrates a schematic diagram of a mouse skull used as a scattering medium and a resolution object placed underneath it in relation to the experimental proof experiment using biological tissue of the reflection matrix-based multiple scattering tracing algorithm according to an embodiment of the present disclosure.

Referring to a schematic diagram 1200 of FIG. 12A, a resolution target object 1201 is placed under a mouse skull tissue 1202 with a thickness of 200 μm, and a reflection matrix based on light incident and reflected through an objective lens 1203 is measured.

since the sample of the schematic diagram 1200 does not have a multi-layer structure unlike the case of the schematic diagram 1100 described in FIG. 11A, there is a need to first find out the location of the phase plane and the number of planes required.

Figure 12B:
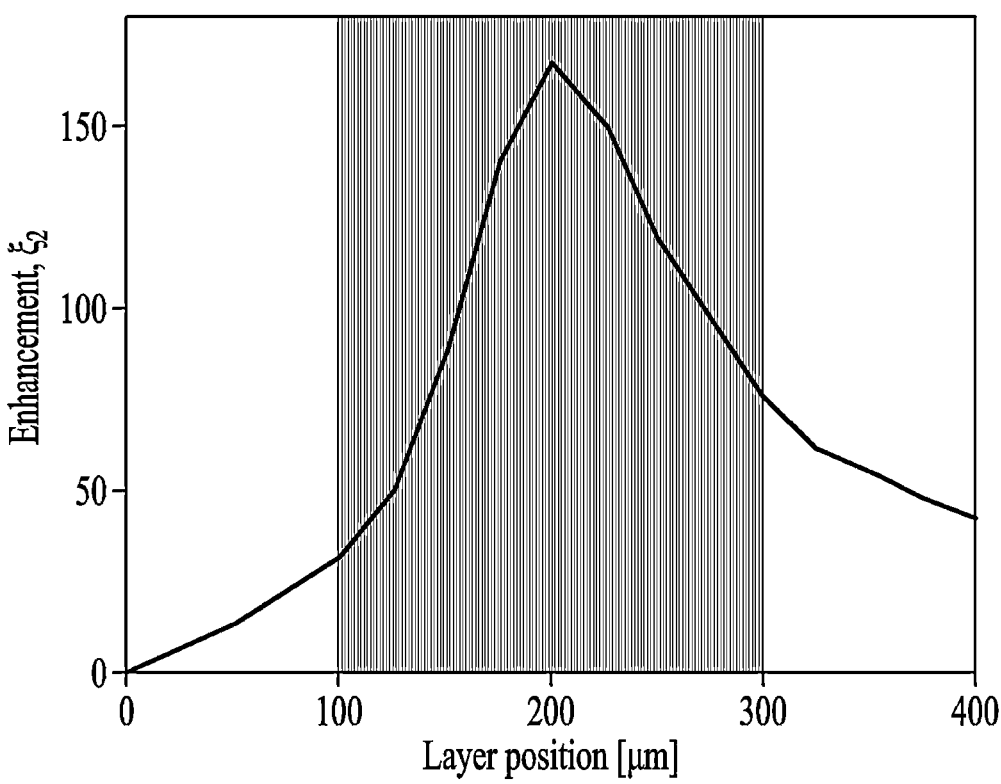

FIG. 12B illustrates a result of an experiment to confirm the position of the phase plane when the sample is not a multilayer structure in relation to the experimental proof experiment using biological tissue of the reflection matrix-based multiple scattering tracing algorithm according to an embodiment of the present disclosure.

Graph 1210 of FIG. 12B is a result dependent upon the position of the phase plane layer, and shows a result of measuring the electric field strength while changing the distance (position) from the target object of the corresponding phase plane and applying the multiple scattering tracing algorithm, assuming a single phase plane.

Graph 1210 shows a result of plotting the total intensity of the image according to the position of the phase plane layer as a function of distance.

In graph 1210, it can be seen that the signal intensity distribution is located in the shaded area, which indicates that the skull tissue is distributed in the location.

Figure 12C:
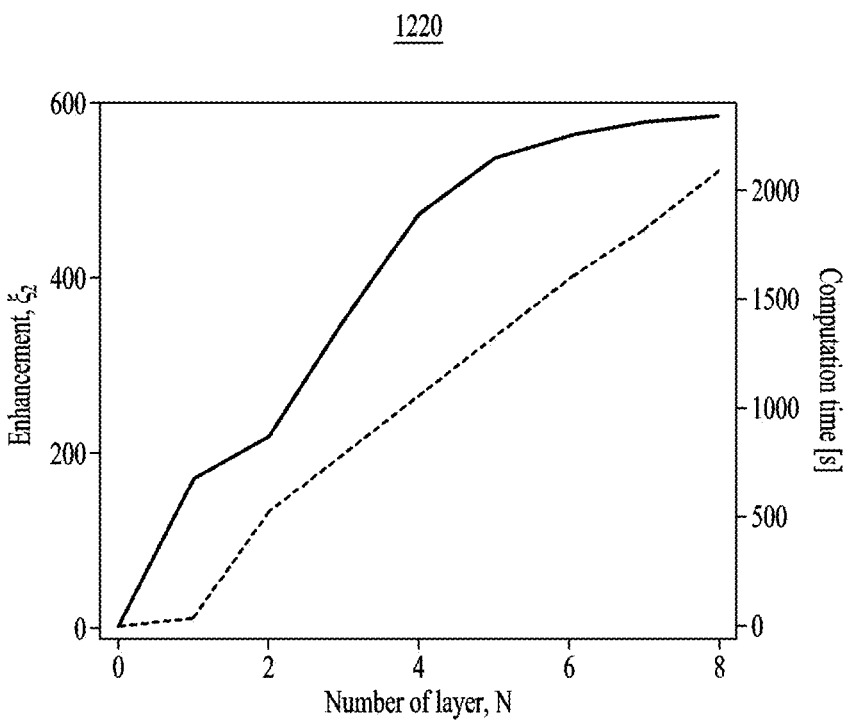

FIG. 12c illustrates a result of an experiment to confirm the number of phase planes when the sample does not have a multilayer structure in relation to the experimental proof experiment using biological tissue of the reflection matrix-based multiple scattering tracing algorithm according to an embodiment of the present disclosure.

Referring to FIG. 12c, graph 1220 shows results of measuring the intensity of the electric field while applying the multiple scattering tracing algorithm based on a change in the number of phase plane layers.

That is, graph 1220 shows results of plotting the signal intensity distribution after applying the multiple scattering tracing algorithm assuming 0 to up to 8 phase planes located inside the area (100 to 300 μm area) based on graph 1210.

Graph 1220 confirms that the signal intensity increases as the number of phase planes increases, but the increase in signal intensity slows down at around 5.

This means that the skull tissue is well approximated by about 5 phase planes.

In addition, the signal intensity increases up to 600 times, which may be a result of using multiple scattering rather than ballistic sound waves for imaging.

Figure 12D:
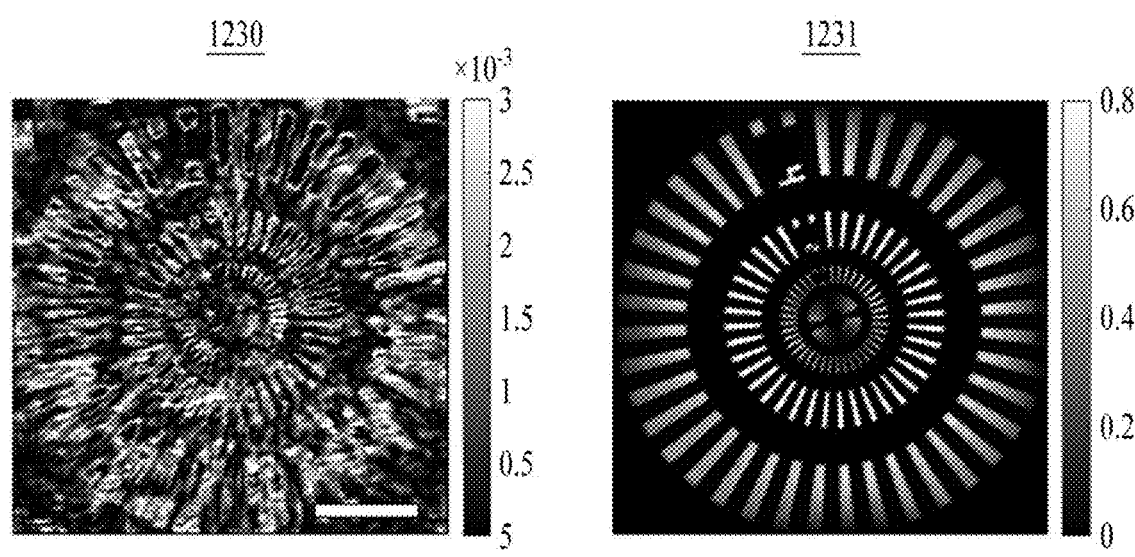

FIG. 12D illustrates a confocal image and a reconstructed image in relation to the experimental proof experiment using biological tissue of the reflection matrix-based multiple scattering tracing algorithm according to an embodiment of the present disclosure.

A confocal image 1230 of FIG. 12D is a confocal image of an object reconstructed from a reflection matrix of a sample and represents an image to which the multiple scattering tracing algorithm is not applied.

Meanwhile, a reconstructed image 1231 may represent an image of a target object reconstructed by the multiple scattering tracing algorithm according to an embodiment of the present disclosure.

Comparing the confocal image 1230 and the reconstructed image 1231, it is proven that the image of the target object is properly restored despite the multiple scattering of the non-multilayered thick skull tissue, which means that the multiple scattering tracking algorithm can be applied to general biological tissues rather than multilayer structures.

FIGS. 13A to 13D illustrate in-vivo imaging results obtained using the reflection matrix-based multiple scattering tracing algorithm according to an embodiment of the present disclosure.

Figure 13A:
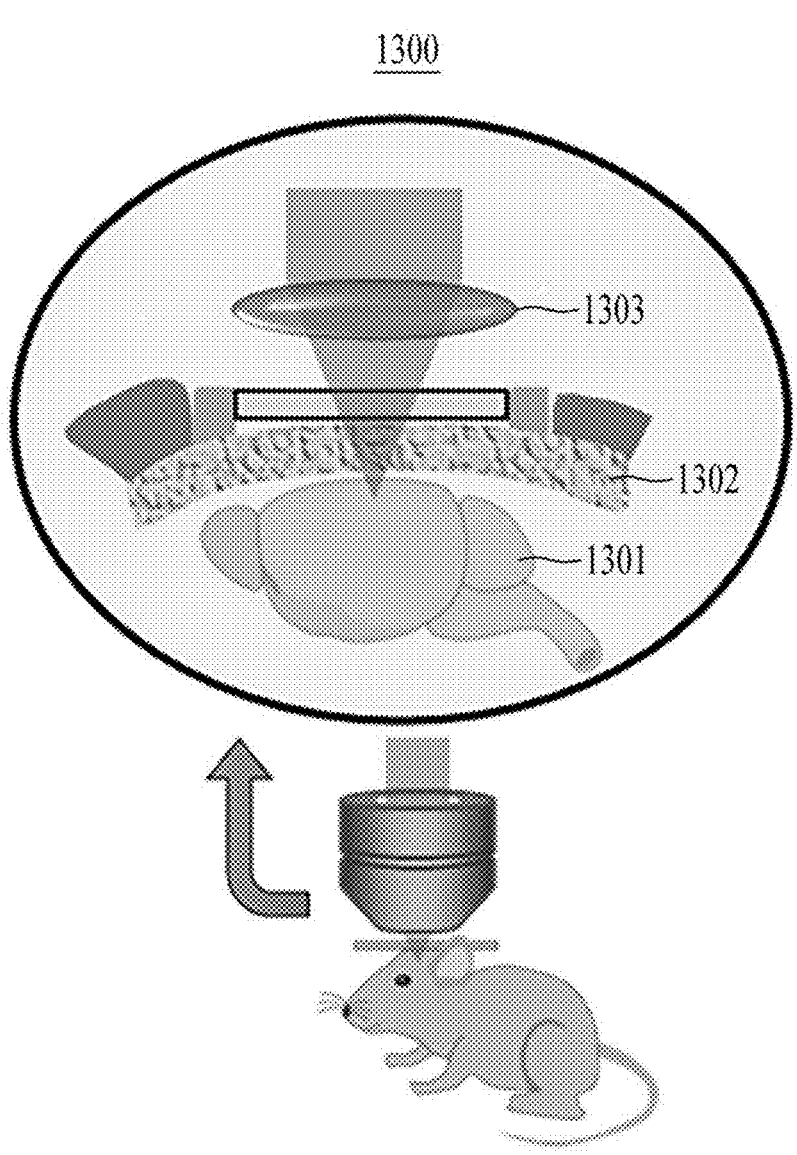

FIG. 13A illustrates a schematic diagram for imaging the skull of a living mouse and the brain cortex therebeyond in relation to the in-vivo imaging results using the reflection matrix-based multiple scattering tracing algorithm according to an embodiment of the present disclosure.

Referring to the schematic diagram 1300 according to an embodiment of the present disclosure of FIG. 13A, light is incident on a specific point of a target object 1301 using an objective lens 1303 so as to image the mouse brain cortex corresponding to the target object 1301 beyond the skull corresponding to a scattering medium 1302.

Figure 13B:
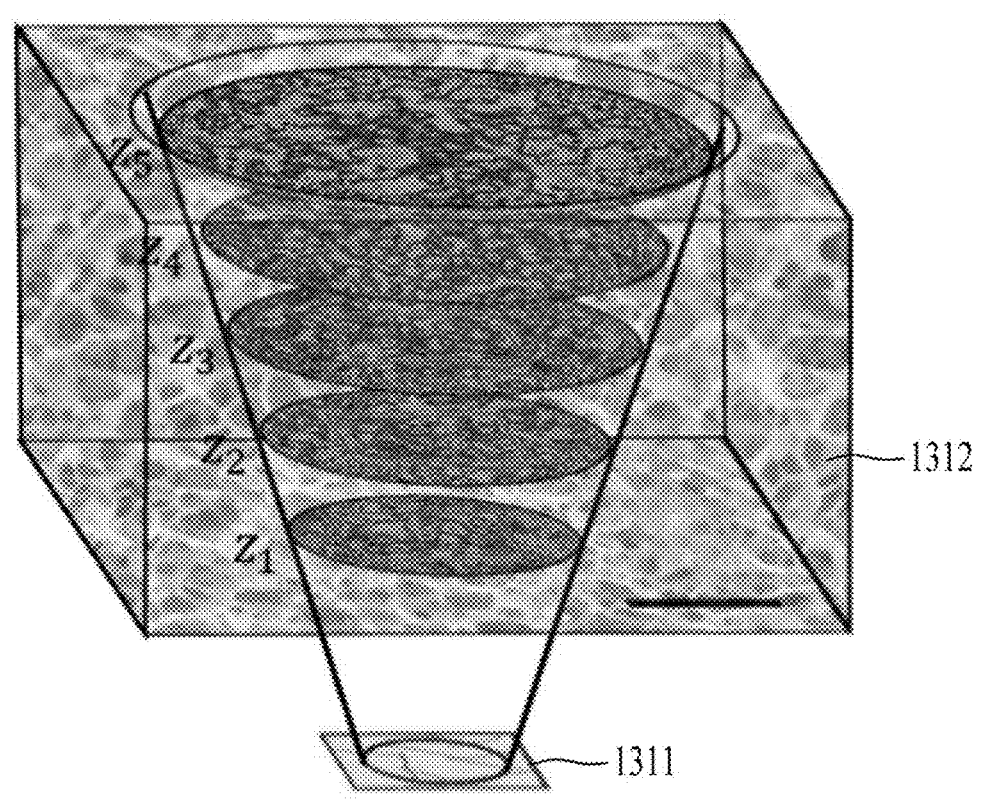

FIG. 13b illustrates an in-vivo imaging result using the reflection matrix-based multiple scattering tracing algorithm according to an embodiment of the present disclosure, and illustrates a schematic diagram of a depth-wise cross-section of the skull and brain cortex of a mouse using a reflection matrix microscope to which the multiple scattering tracing algorithm is applied.

Referring to FIG. 13b, a schematic diagram 1310 schematically depicts the brain, which is a target object 1311, and the skull, which corresponds to a scattering medium 1312.

According to the reflection matrix-based multiple scattering tracing algorithm according to an embodiment of the present disclosure, a plurality of phase planes are located within the scattering medium 1312 to compensate for multiple scattering distortion according to the scattering trajectory caused by multiple scattering components of the scattering medium 1312.

For example, the plural phase planes are composed of a first phase plane ($z_1$) to a fifth phase plane ($z_5$) based on the target object 1311.

The number of the plural phase planes is proportional to the complexity due to multiple scattering components of the scattering medium 1312.

That is, the number of plural phase planes increases as complexity increases. As the number of plural phase planes increases, the degree of improvement increases, but calculation time may also increase, so it may be determined to correspond to maximum efficiency.

Figure 13C:
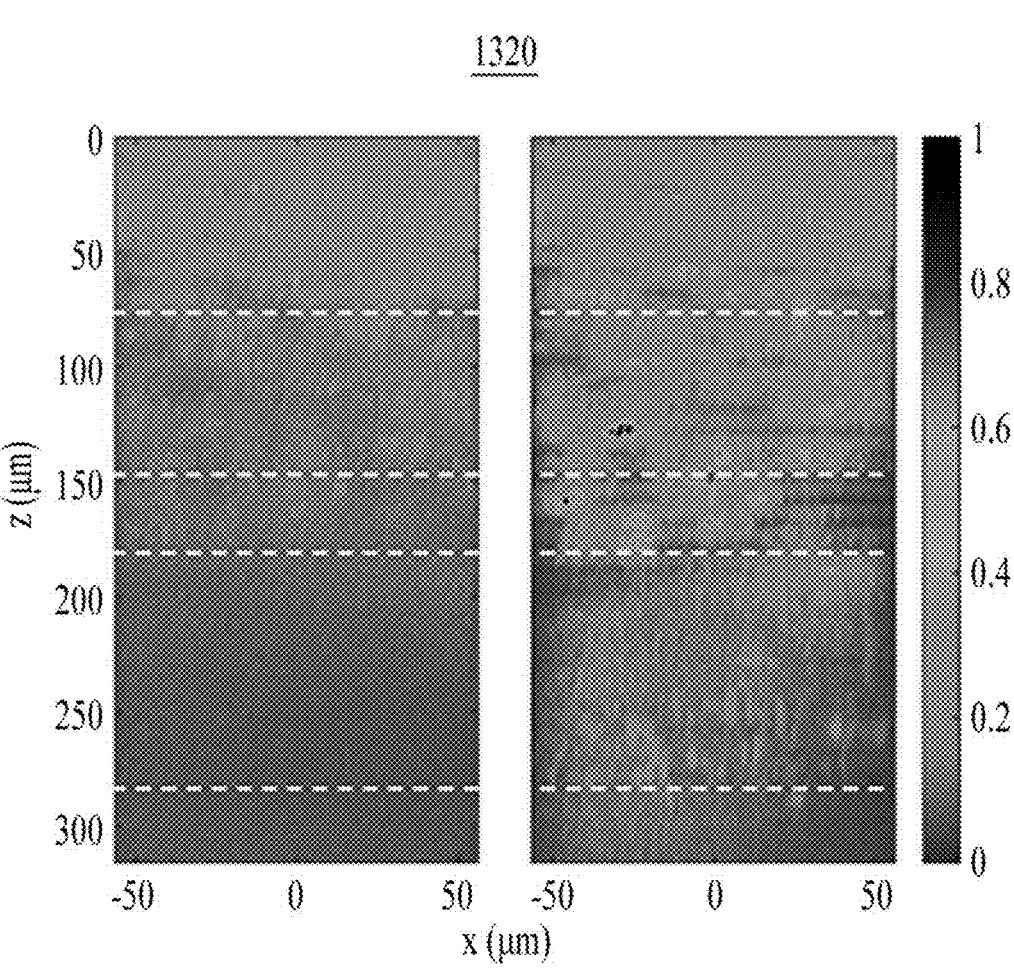

FIG. 13c illustrates an in-vivo imaging result using the reflection matrix-based multiple scattering tracing algorithm according to an embodiment of the present disclosure, and shows a depth-wise cross-section image of the skull and brain cortex of a mouse using a reflection matrix microscope before and after application of the multiple scattering tracing algorithm.

Referring to the image 1320 of FIG. 13c, the signal intensity decreases rapidly after 60 μm inside the skull in the confocal image before applying the multiple scattering tracking algorithm. On the other hand, the specific internal shape is revealed up to a depth of 300 μm after applying the multiple scattering tracing algorithm.

In addition, it can be seen from the multi-plane image after applying the multiple scattering tracing algorithm that the boundary between the skull and the brain cortex surface is formed around 200 μm depth.

Figure 13D:
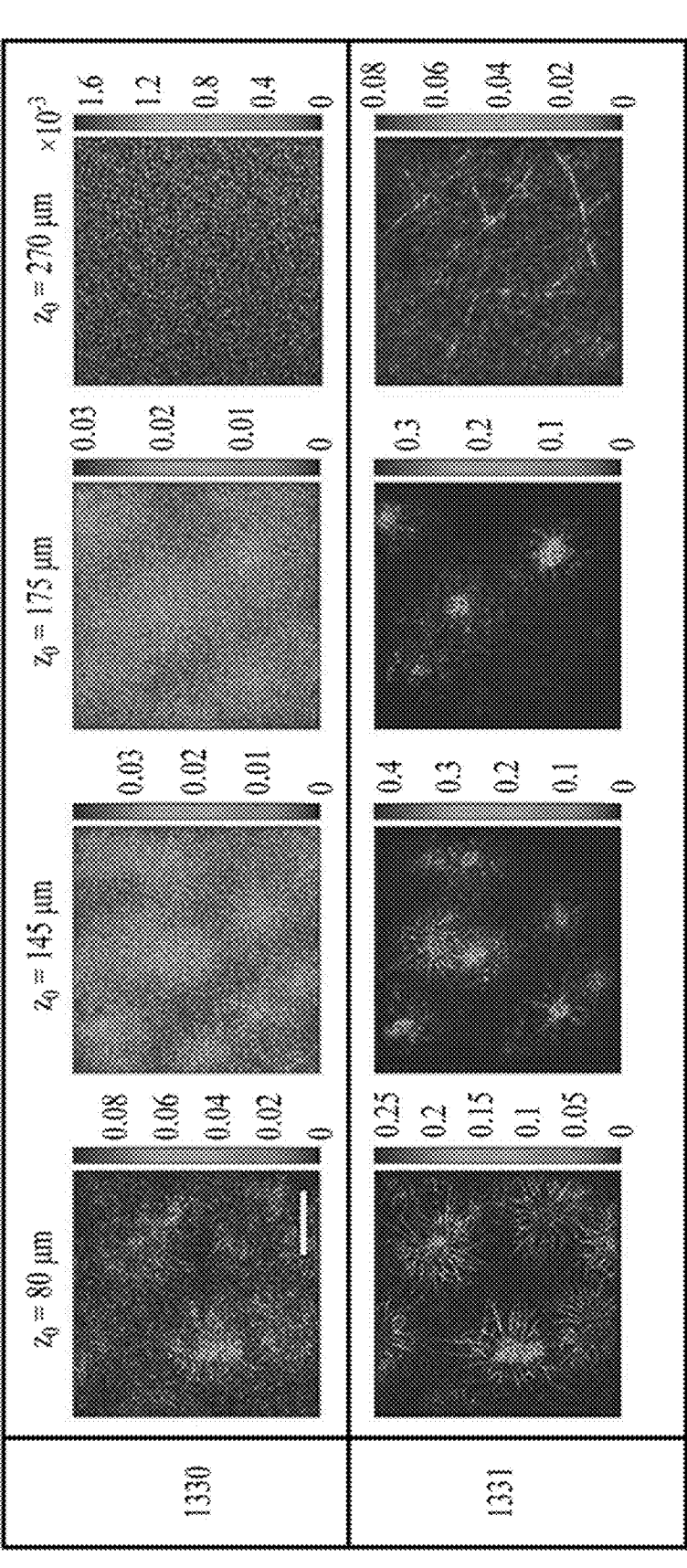

FIG. 13D illustrates a comparison between a confocal image reconstructed from a reflection matrix for each depth and a restored image using the multiple scattering tracking algorithm in relation to the in-vivo imaging results using the reflection matrix-based multiple scattering tracing algorithm according to an embodiment of the present disclosure.

Referring to FIG. 13D, the depth within the scattering medium is divided into four, and the confocal image 1330 on the x-y plane is compared with the reconstructed image 1331 according to an example in the present disclosure.

The first three rows of images in the confocal image 1330 and the reconstructed image 1331 correspond to images inside the skull, and the last row shows images inside the brain cortex. In the case of the confocal image 1330, the specific structures of the cells are distorted due to multiple scattering at a depth of 80 μm, thereby being not visible properly.

In the case of the reconstructed image 1331, the shapes of the osteocytes and canaliculi, which extend from each cell, inside the skull are clearly shown up to the 175 μm area at the bottom of the skull.

In addition, the reconstructed image 1331 clearly shows nerve bundles in the brain cortex layer at a depth of 270 μm.

That is, the present disclosure clearly demonstrates that it can be used for in-vivo imaging of living objects, and that the multiple scattering tracing algorithm method can show superior performance compared to an existing confocal microscope.

Accordingly, the present disclosure has a very wide range of uses for image acquisition in a label-free manner, does not require additional equipment required in an existing reflection matrix microscope, and does not affect the data measurement time itself because it is a post-processing technology. So, it is expected to be used for in-vivo image acquisition that requires rapid measurement, and to be used in research on various disease models or animal experiments, and to provide an imaging device and method that can expand the scope of application to use as a diagnostic and clinical tool.

In addition, the present invention is a post-processing method in which data such as reflection matrix data is acquired and then corrected, and immediately acquires data without prior preparation, thereby obtaining 3D high-depth images while maintaining the subject's condition in in-vivo imaging as data measurement time is reduced.

Figure 14:
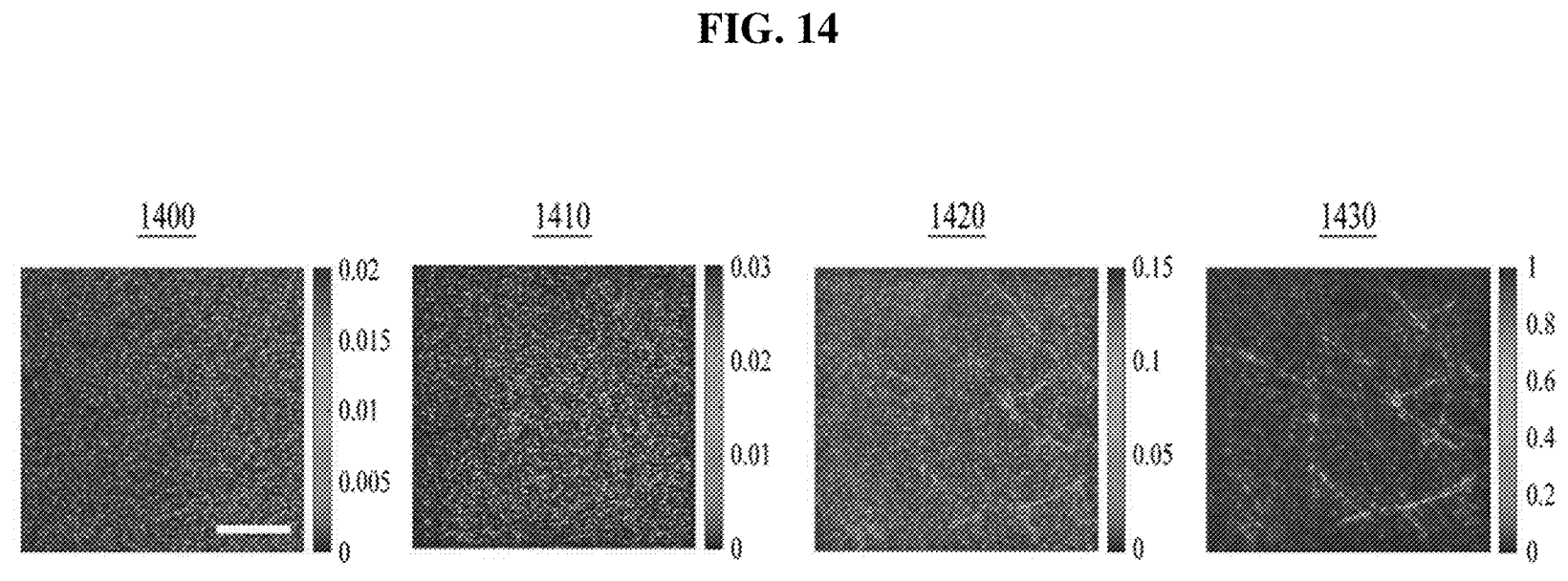

FIG. 14 illustrates the correction and restoration performance of an imaging device for correcting and reconstructing a target image in a scattering medium using the reflection matrix-based multiple scattering tracing algorithm according to an embodiment of the present disclosure.

In FIG. 14, the correction and restoration performance of the imaging device for correcting and reconstructing a target image in a scattering medium using the reflection matrix-based multiple scattering tracing algorithm according to an embodiment of the present disclosure is compared with an existing technology.

Referring to FIG. 14, images 1400 to 1430 illustrate performance comparison results for respective imaging methods of a reflection matrix microscope.

The image 1400 shows a confocal microscope image, the image 1410 shows a CLASS microscope image, the image 1420 shows a conjugate-CLASS image, and the image 1430 shows an image corrected and reconstructed using the multiple scattering tracing algorithm based on a reflection matrix.

The image 1430 may be the corrected and reconstructed image described in FIG. 13.

When comparing the images 1400 to 1430, it can be easily confirmed that the present invention shows relatively superior performance.

This is because the present invention utilizes multiple scattering as an imaging signal while other imaging methods use ballistic sound waves that exponentially decrease with depth. The present invention shows superior restoration and correction performance.

Therefore, the present invention can provide an imaging device and method capable of providing various biomedical applications because it can acquire 3D high-depth images while changing a measurement depth along with a reduction in data measurement time.

In addition, the present invention is an algorithm applied to a reflection matrix obtained through reflection without labeling, and provides an imaging device that can be directly applied to clinical practice because it can acquire high-depth, high-resolution images, and that can be applied as measurement equipment because it can obtain images of the inside of not only biological tissues but also samples such as semiconductors without disassembling the inside.

The present disclosure can provide a device for tracing multiple scattering trajectories using a time-resolved reflection matrix obtained from an imaging device using a time-resolved light source, and then correcting and reconstructing an internal target image located deep inside a scattering medium such as biological tissue by correcting the traced multiple scattering trajectory; and a method thereof.

The present disclosure can obtain a time-resolved reflection matrix of the scattering medium, and then reconstruct the trajectory of multiple scattered waves using a numerical iterative technique according to the multiple scattering tracing (MST) algorithm, and reconstruct and correct a target image corresponding to an object inside a scattering medium image using the reverse process of the trajectory of the reconstructed multiple scattering waves.

The present disclosure has a very wide range of uses for image acquisition in a label-free manner, does not require additional equipment required in an existing reflection matrix microscope, and does not affect the data measurement time itself because it is a post-processing technology. So, it is expected to be used for in-vivo image acquisition that requires rapid measurement, and to be used in research on various disease models or animal experiments, and provides an imaging device and method that can expand the scope of application to use as a diagnostic and clinical tool.

The present invention is a post-processing method in which data such as reflection matrix data is acquired and then corrected, and immediately acquires data without prior preparation, thereby obtaining 3D high-depth images while maintaining the subject's condition in in-vivo imaging as data measurement time is reduced.

The present invention can provide an imaging device and method capable of providing various biomedical applications because it can acquire 3D high-depth images while changing a measurement depth along with a reduction in data measurement time.

The present invention is an algorithm applied to a reflection matrix obtained through reflection without labeling, and provides an imaging device that can be directly applied to clinical practice because it can acquire high-depth, high-resolution images, and that can be applied as measurement equipment because it can obtain images of the inside of not only biological tissues but also samples such as semiconductors without disassembling the inside.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of executing and responding to instructions. The processing device may execute an operating system (OS) and one or more software applications executing on the operating system. In addition, the processing device may access, store, manipulate, process, and generate data in response to execution of the software. For ease of understanding, the processing apparatus may be described as being used singly, but those skilled in the art will recognize that the processing apparatus may include a plurality of processing elements and/or a plurality of types of processing elements. For example, the processing apparatus may include a plurality of processors or one processor and one controller. Other processing configurations, such as a parallel processor, are also possible.

The software may include computer programs, code, instructions, or a combination of one or more of the foregoing, configure the processing apparatus to operate as desired, or command the processing apparatus, either independently or collectively. In order to be interpreted by a processing device or to provide instructions or data to a processing device, the software and/or data may be embodied permanently or temporarily in any type of a machine, a component, a physical device, a virtual device, a computer storage medium or device, or a transmission signal wave. The software may be distributed over a networked computer system and stored or executed in a distributed manner. The software and data may be stored in one or more computer-readable recording media.

Although the present disclosure has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

What is claimed is:

1. An imaging device, comprising:
a light source configured to make light incident on a target object by passing through a scattering medium and multiple scattering components within the scattering medium;
a detector configured to detect light returned after the incident light transmits and reflects the multiple scattering components of the target object;
a reflection matrix measurer configured to measure a time-resolved reflection matrix reflecting multiple scattering trajectories based on the multiple scattering components based on the returning light;
an algorithm processor configured to obtain an incident transmission matrix and a reflection transmission matrix by numerically iteratively accessing a plurality of phase planes approximated from the scattering medium according to a multiple scattering tracing algorithm and to obtain an object reflection matrix by reflecting inverse matrices of the obtained incident transmission matrix and the obtained reflection transmission matrix into the measured time-resolved reflection matrix; and
an image processor configured to acquire an image in which multiple scattering distortion is corrected according to the multiple scattering trajectory based on the obtained object reflection matrix.

2. The imaging device according to claim 1, wherein the algorithm processor performs numerical iterative access to each phase plane by multiplying an input or output end of the time-resolved reflection matrix by a spatial propagation matrix ($P_k$) corresponding to a distance to a k-th phase plane based on the multiple scattering tracing algorithm to obtain a plurality of incident transmission matrices and reflection transmission matrices corresponding to the k-th.

3. The imaging device according to claim 1, wherein, in consideration of a case where light is focused on two different points for a specific phase plane among the plural phase planes, the algorithm processor obtains a difference between phase delay values of the two points based on the multiple scattering tracing algorithm, and applies the obtained difference to an incident transmission matrix and reflection transmission matrix obtained for the specific phase plane.

4. The imaging device according to claim 1, wherein each of the plural phase planes calculates a transmission matrix in relation to the multiple scattering components inside the scattering medium, designs a first phase plane based on the calculated transmission matrix, and designs a second phase plane on the designed first phase plane based on the inverse transmission matrix of the calculated transmission matrix to be virtually located inside the scattering medium or to be located on the scattering medium.

5. The imaging device according to claim 1, wherein a location of the plural phase planes is determined by measuring an electric field intensity through application of the multiple scattering tracing algorithm while changing a distance from the target object, and is determined as a location where the measured electric field intensity is greater than a reference value.

6. The imaging device according to claim 1, wherein the number of the plural phase planes is determined by measuring an electric field strength through application of the multiple scattering tracing algorithm while changing the number of phase planes, and is determined considering a calculation time according to the changed number.

7. The imaging device according to claim 1, wherein the reflection matrix measurer determines matrix components as light concentrated at each position on a surface of the target object, and measures the time-resolved reflection matrix determined as an intensity and phase of electric field measured on an output basis at each position of a camera placed on a conjugate image plane of the object surface, resulting in reflected light on an input basis.

8. The imaging device according to claim 1, wherein the light source makes the light incident as a point light on the target object and changes an incident location on the target object by changing a position of the point light, and
the detector detects the changed detection pixel according to the changed incident location.

9. The imaging device according to claim 1, wherein the algorithm processor calculates an inverse matrix for each of an incident transmission matrix and reflection transmission matrix associated with phase values for the plural phase planes for the multiple scattering components of the scattering medium according to the multiple scattering tracing algorithm and phase values for plural points respectively constituting the plural phase planes, and reflects the calculated inverse matrix into the time-resolved reflection matrix to obtain an object reflection matrix for the target object.

10. An imaging method, comprising:
making, by a light source, light incident on a target object by passing through a scattering medium and multiple scattering components within the scattering medium;
detecting, by a detector, light returned after the incident light transmits and reflects the multiple scattering components of the target object;
measuring, by a reflection matrix measurer, a time-resolved reflection matrix reflecting multiple scattering trajectories based on the multiple scattering components based on the returning light;
obtaining, by an algorithm processor, an incident transmission matrix and a reflection transmission matrix by numerically iteratively accessing a plurality of phase planes approximated from the scattering medium according to a multiple scattering tracing algorithm and obtaining an object reflection matrix by reflecting inverse matrices of the obtained incident transmission matrix and the obtained reflection transmission matrix into the measured time-resolved reflection matrix; and
acquiring, by an image processor, an image in which multiple scattering distortion is corrected according to the multiple scattering trajectory based on the obtained object reflection matrix.

11. The imaging method according to claim 10, wherein the obtaining comprises performing numerical iterative access to each phase plane by multiplying an input or output end of the time-resolved reflection matrix by a spatial propagation matrix ($P_k$) corresponding to a distance to a k-th phase plane based on the multiple scattering tracing algorithm to obtain a plurality of incident transmission matrices and reflection transmission matrices corresponding to the k-th.

12. The imaging method according to claim 10, wherein the obtaining comprises obtaining, in consideration of a case where light is focused on two different points for a specific phase plane among the plural phase planes, a difference between phase delay values of the two points based on the multiple scattering tracing algorithm, and applying the obtained difference to an incident transmission matrix and reflection transmission matrix obtained for the specific phase plane.

13. The imaging method according to claim 10, wherein each of the plural phase planes calculates a transmission matrix in relation to the multiple scattering components inside the scattering medium, designs a first phase plane based on the calculated transmission matrix, and designs a second phase plane on the designed first phase plane based on the inverse transmission matrix of the calculated transmission matrix to be virtually located inside the scattering medium or to be located on the scattering medium.

14. The imaging method according to claim 10, wherein a location of the plural phase planes is determined by measuring an electric field intensity through application of the multiple scattering tracing algorithm while changing a distance from the target object, and is determined as a location where the measured electric field intensity is greater than a reference value, and the number of the plural phase planes is determined by measuring an electric field strength through application of the multiple scattering tracing algorithm while changing the number of phase planes, and is determined considering a calculation time according to the changed number.

\* \* \* \* \*